United States Patent
Semenov

(10) Patent No.: US 10,492,700 B2
(45) Date of Patent: Dec. 3, 2019

(54) METHODS OF ASSESSING THE NORMALCY OF BIOLOGICAL TISSUE

(71) Applicant: EMTensor GmbH, Vienna (AT)

(72) Inventor: Serguei Y Semenov, Vienna (AT)

(73) Assignee: EMTensor GmbH, Vienna (AT)

( * ) Notice: Subject to any disclaimer, the term of this patent is extended or adjusted under 35 U.S.C. 154(b) by 1062 days.

(21) Appl. No.: 14/788,042

(22) Filed: Jun. 30, 2015

(65) Prior Publication Data

US 2015/0342472 A1    Dec. 3, 2015

Related U.S. Application Data

(63) Continuation of application No. 13/894,401, filed on May 14, 2013, now abandoned.
(Continued)

(51) Int. Cl.
*A61B 5/0265* (2006.01)
*A61B 5/053* (2006.01)
(Continued)

(52) U.S. Cl.
CPC ............ *A61B 5/0265* (2013.01); *A61B 5/004* (2013.01); *A61B 5/0295* (2013.01); *A61B 5/053* (2013.01);
(Continued)

(58) Field of Classification Search
CPC ....... A61B 5/0265; A61B 5/027; A61B 5/004; A61B 5/0295; A61B 5/05; A61B 5/0507;
(Continued)

(56) References Cited

U.S. PATENT DOCUMENTS 4,135,131 A    1/1979 Larsen et al.
4,157,472 A    6/1979 Beck, Jr. et al.
(Continued)

FOREIGN PATENT DOCUMENTS

EP    2404550 A1    1/2012
EP    2404550 B1    11/2015
(Continued)

OTHER PUBLICATIONS

Rompelman, O., and H. H. Ros. "Coherent averaging technique: A tutorial review Part 1: Noise reduction and the equivalent filter." Journal of biomedical engineering 8, No. 1 (1986): 24-29.*
(Continued)

*Primary Examiner* — Carolyn A Pehlke
(74) *Attorney, Agent, or Firm* — Tillman Wright, PLLC; James D. Wright; David R. Higgins

(57) ABSTRACT

A method of assessing status of a biological tissue includes irradiating an electromagnetic signal, via a probe, into a biological tissue. The irradiated electromagnetic signal is received after being scattered/reflected by the biological tissue. Blood flow information pertaining to the biological tissue is provided, and the received signal is analyzed based at least upon the provided blood flow information and upon knowledge of electromagnetic signal differences in normal, suspicious, and abnormal tissue. Using a dielectric properties reconstruction algorithm, dielectric properties of the biological tissue are reconstructed based at least upon results of the analyzing step and upon blood flow information, and using a tissue properties reconstruction algorithm, tissue properties of the biological tissue are reconstructed based at least in part upon results of the reconstructing step and upon blood flow information.

20 Claims, 18 Drawing Sheets

Related U.S. Application Data

(60) Provisional application No. 61/802,339, filed on Mar. 15, 2013.

(51) Int. Cl.
*A61B 5/00* (2006.01)
*A61B 5/0295* (2006.01)
*A61B 5/05* (2006.01)
*A61B 5/0456* (2006.01)

(52) U.S. Cl.
CPC .......... *A61B 5/0507* (2013.01); *A61B 5/7246* (2013.01); *A61B 5/7278* (2013.01); *A61B 5/7282* (2013.01); *A61B 5/0456* (2013.01); *A61B 5/7289* (2013.01); *A61B 2560/0431* (2013.01); *A61B 2576/02* (2013.01)

(58) Field of Classification Search
CPC ..... A61B 5/053; A61B 5/7246; A61B 5/7278; A61B 5/7282
See application file for complete search history.

(56) References Cited

U.S. PATENT DOCUMENTS

| | | | |
|---|---|---|---|
| 4,247,815 A | 1/1981 | Larsen et al. | |
| 4,257,278 A * | 3/1981 | Papadofrangakis | A61B 8/06 73/861.25 |
| 4,638,813 A | 1/1987 | Turner | |
| 4,662,222 A | 5/1987 | Johnson | |
| 4,798,209 A | 1/1989 | Klingenbeck et al. | |
| 4,805,627 A | 2/1989 | Klingenbeck et al. | |
| 4,926,868 A | 5/1990 | Larsen | |
| 5,069,223 A | 12/1991 | McRae | |
| 5,222,501 A | 6/1993 | Ideker et al. | |
| 5,233,713 A | 8/1993 | Murphy et al. | |
| 5,263,050 A | 11/1993 | Sutterlin et al. | |
| 5,305,748 A | 4/1994 | Wilk | |
| 5,363,050 A | 11/1994 | Guo et al. | |
| 5,405,346 A | 4/1995 | Grundy et al. | |
| 5,715,819 A | 2/1998 | Svenson et al. | |
| 5,800,350 A * | 9/1998 | Coppleson | A61B 5/0059 600/372 |
| 6,026,173 A | 2/2000 | Svenson et al. | |
| 6,073,047 A | 6/2000 | Barsamian et al. | |
| 6,332,087 B1 | 12/2001 | Svenson et al. | |
| 6,333,087 B1 | 12/2001 | Jerdee et al. | |
| 6,490,471 B2 | 12/2002 | Svenson et al. | |
| 6,503,203 B1 | 1/2003 | Rafter et al. | |
| 6,511,427 B1 * | 1/2003 | Sliwa, Jr. | A61B 5/4869 600/438 |
| 6,522,910 B1 | 2/2003 | Gregory | |
| 6,697,660 B1 | 2/2004 | Robinson | |
| 6,865,494 B2 | 3/2005 | Duensing et al. | |
| 7,239,731 B1 | 7/2007 | Semenov et al. | |
| 7,272,431 B2 | 9/2007 | McGrath | |
| 7,340,292 B2 | 3/2008 | Li | |
| 7,876,114 B2 | 1/2011 | Campbell et al. | |
| 8,000,775 B2 | 8/2011 | Pogue et al. | |
| 8,089,417 B2 | 1/2012 | Popovic et al. | |
| 8,207,733 B2 | 6/2012 | Meaney et al. | |
| 8,253,619 B2 | 8/2012 | Holbrook et al. | |
| 8,376,948 B2 | 2/2013 | Brannan | |
| 8,708,919 B1 | 4/2014 | Frazier | |
| 8,724,864 B2 | 5/2014 | Persson et al. | |
| 9,072,449 B2 | 7/2015 | Semenov | |
| 9,414,749 B2 | 8/2016 | Semenov | |
| 9,414,763 B2 | 8/2016 | Semenov | |
| 9,414,764 B2 | 8/2016 | Semenov | |
| 9,675,254 B2 | 6/2017 | Semenov | |
| 9,675,255 B2 | 6/2017 | Semenov | |
| 9,724,010 B2 | 8/2017 | Semenov | |
| 2002/0017905 A1 | 2/2002 | Conti | |
| 2002/0168317 A1 | 11/2002 | Daighighian et al. | |
| 2002/0191744 A1 | 12/2002 | Mirabella | |
| 2003/0018244 A1 | 1/2003 | Haddad et al. | |
| 2003/0088180 A1 | 5/2003 | Van Veen et al. | |
| 2003/0090276 A1 | 5/2003 | Weide et al. | |
| 2004/0123667 A1 | 7/2004 | McGrath | |
| 2004/0174948 A1 | 9/2004 | Kojima et al. | |
| 2004/0220465 A1 * | 11/2004 | Cafarella | A61B 5/0091 600/407 |
| 2005/0135560 A1 | 6/2005 | Dafni et al. | |
| 2006/0133564 A1 | 6/2006 | Langan et al. | |
| 2006/0247531 A1 | 11/2006 | Pogue et al. | |
| 2006/0276714 A1 | 12/2006 | Holt et al. | |
| 2007/0025514 A1 | 2/2007 | Lawaczeck | |
| 2007/0238957 A1 | 10/2007 | Yared | |
| 2008/0319437 A1 | 12/2008 | Turner et al. | |
| 2009/0015832 A1 | 1/2009 | Popovic et al. | |
| 2009/0292195 A1 | 11/2009 | Boyden et al. | |
| 2010/0010340 A1 | 1/2010 | Godavarty et al. | |
| 2010/0067770 A1 | 3/2010 | Persson et al. | |
| 2010/0174179 A1 | 7/2010 | Persson et al. | |
| 2011/0022325 A1 | 1/2011 | Craddock et al. | |
| 2011/0263961 A1 | 10/2011 | Craddock et al. | |
| 2011/0295102 A1 | 12/2011 | Lakkis et al. | |
| 2012/0010493 A1 | 1/2012 | Semenov | |
| 2012/0083683 A1 | 4/2012 | Kuwabara | |
| 2012/0083690 A1 | 4/2012 | Semenov | |
| 2012/0172954 A1 | 7/2012 | Zastrow et al. | |
| 2012/0179037 A1 | 7/2012 | Halmann | |
| 2012/0190977 A1 | 7/2012 | Persson et al. | |
| 2013/0002264 A1 | 1/2013 | Gaerber | |
| 2013/0257426 A1 | 10/2013 | Feiweier et al. | |
| 2014/0024917 A1 | 1/2014 | McMahon et al. | |
| 2014/0155740 A1 | 6/2014 | Semenov | |
| 2014/0275944 A1 | 9/2014 | Semenov | |
| 2014/0276012 A1 | 9/2014 | Semenov | |
| 2014/0378812 A1 | 12/2014 | Saroka et al. | |
| 2015/0257648 A1 | 9/2015 | Semenov | |
| 2015/0257649 A1 | 9/2015 | Semenov | |
| 2016/0256109 A1 | 9/2016 | Semenov | |
| 2016/0262623 A1 | 9/2016 | Semenov | |
| 2016/0324489 A1 | 11/2016 | Crawford et al. | |
| 2016/0345856 A1 | 12/2016 | Semenov | |
| 2017/0273563 A1 | 9/2017 | Semenov | |
| 2018/0235486 A1 | 8/2018 | Semenov | |

FOREIGN PATENT DOCUMENTS

| | | |
|---|---|---|
| EP | 3037035 A1 | 6/2016 |
| IL | 241603 | 10/2016 |
| IL | 245691 | 2/2017 |
| IL | 245691 | 5/2017 |
| IL | 213937 | 8/2017 |
| RU | 2449729 C2 | 5/2012 |
| RU | 2011128101 A | 1/2013 |
| RU | 2596984 C2 | 9/2016 |
| RU | 2603613 C1 | 11/2016 |
| RU | 2015144025 A | 4/2017 |
| WO | 9532665 | 12/1995 |
| WO | 199852464 A1 | 11/1998 |
| WO | 200015109 A1 | 3/2000 |
| WO | 00/64343 A1 | 11/2000 |
| WO | 2005115235 A1 | 12/2005 |
| WO | 2007136334 A1 | 11/2007 |
| WO | 2008002251 A1 | 1/2008 |
| WO | 2010100649 A1 | 9/2010 |
| WO | 2011009945 A2 | 1/2011 |
| WO | 2011156810 A2 | 12/2011 |
| WO | 2011156810 A3 | 12/2011 |
| WO | 2013005134 A2 | 1/2013 |
| WO | 2013005134 A3 | 1/2013 |
| WO | 2014081992 A2 | 5/2014 |
| WO | 2014150616 A2 | 9/2014 |
| WO | 2014150618 A1 | 9/2014 |
| WO | 2014150616 A3 | 12/2014 |

(56) References Cited

FOREIGN PATENT DOCUMENTS

WO    2014081992 A3    8/2015
WO    2017066731 A1    4/2017

OTHER PUBLICATIONS

Information Disclosure Statement (IDS) Letter Regarding Common Patent Application(s), dated Dec. 7, 2017.
"International Search Report" and "Written Opinion of the International Searching Authority" (ISA/US) in Emtensor GmbH, International Patent Application Serial No. PCT/US2016/057254, dated Jan. 12, 2017 (7 pages).
Abubakar, A.; van den Berg, P.M. and Mallorqui, J.J. (2002). "Imaging of biomedical data using a multiplicative regularized contrast source inversion method", IEEE Transactions of Microwave Theory and Techniques 50 : 1761-1771. (10 pages).
Bulyshev, A.E.; Souvorov, A.E.; Semenov, S. Y. ; Posukh, V.G. and Sizov, Y. E. (2004). "Three-dimensional vector microwave tomography: theory and computational experiments", Inverse Problems 20 : 1239.
Bulyshev, A.E.; Souvorov, A. E.; Semenov, S.Y.; Svenson, R.H.; Nazarov, A.G.; Sizov, Y.E. and Tatsis, G. P. (2000) "Three-dimensional microwave tomography. Theory and computer experiments in scalar approximation", Inverse Problems 16 : 863.
Chew, W. C. and Wang, Y. M. (1990). "Reconstruction of two-dimensional permittivity distribution using the distorted Born iterative method", IEEE Transactions on Medical Imaging 9 : 218-225. (8 pages).
Devaney, A. J. (1992). Current research topics in diffraction tomography. In: Bertero, M. & Pike, E. (Ed.), Inverse Problems in Scattering and Imaging, Adam Hilger, New York.
Harada, H.; Wall, D. J. N.; Takenaka, T. and Tanaka, M. (1995). "Conjugate gradient method applied to inverse scattering problem", IEEE Transactions on Antennas and Propagation 43 : 784-792. (9 pages).
Joachimowicz, N.; Mallorqui, J. J.; Bolomey, J. C. and Broquets, A. (1998). "Convergence and stability assessment of Newton-Kantorovich reconstruction algorithms for microwave tomography," IEEE Transactions on Medical Imaging 17 : 562-570. (9 pages).
Kleinman, R. and den Berg, P. (1992). "A modified gradient method for two- dimensional problems in tomography," Journal of Computational and Applied Mathematics 42 : 17-35.
Lobel P.; Kleinman, R. E; Pichot, C.; Blanc-Feraud, L. and Barlaud, M. (1996). "Conjugate-Gradient Method for Soliving Inverse Scattering with Experimental Data", IEEE Antennas and Propagation Magazine 38 : 48.
Meaney, P. M.; Paulsen, K. D.; Hartov, A. and Crane, R. K. (1996). "Microwave imaging for tissue assessment: initial evaluation in multitarget tissue-equivalent phantoms", IEEE Transactions on Biomedical Engineering 43 : 878-890. (12 pages).
Semenov, S. Y.; Bulyshev, A. E.; Abubakar, A.; Posukh, V. G.; Sizov, Y. E.; Souvorov, A. E; van den Berg, P. M. and Williams, T. C. (2005). Microwave-tomographic imaging of the high dielectric-contrast objects using different imagereconstruction approaches, IEEE Transactions on Microwave Theory and Techniques 53 : 2284-2294. (10 pages).
Semenov, S. Y.; Bulyshev, A. E.; Souvorov, A. E.; Svenson, R. H.; Sizov, Y. E; Vorisov, V. Y.; Posukh, V. G.; Kozlov, I. M.; Nazarov, A. G. And Tatsis, G. P. (1998). Microwave tomography: theoretical and experimental investigation of the iteration reconstruction algorithm, IEEE Transactions on Microwave Theory and Techniques 46 : 133-141 (9 pages).
Semenov, S. Y.; Bulyshev, A. E.; Posukh, V. G.; Sizov, Y. E.; Williams, T. C. and Souvorov, A. E. (2003). Microwave Tomography for Detection/Imaging of Myocardial Infarction. I. Excised Canine Hearts, Annals of Biomedical Engineering 31 : 262-270. (9 pages).

Semenov, S.Y.; Kellam, J.; Althausen, P.; Williams, T.; Abubakar, A.; Bulyshev, A.; Sizov, Y. (2007) "Microwave tomography for functional imaging of extremity soft tissues: feasibility assessment." Physics in Medicine and Biology, doi: 10.1088/0031-9155/52/18/015. (15 pages).
Souvorov, A. E.; Bulyshev, A. E.; Semenov, S. Y.; Svenson, R. H.; Nazarov, A. G.; Sizov, Y. E. and Tatsis, G. P. (1998). Microwave tomography: a two-dimensional Newton iterative scheme, IEEE Transactions on Microwave Theory and Techniques 46 : 1654-1659. (6 pages).
Information Disclosure Statement (IDS) Letter Regarding Common Patent Application(s), dated May 26, 2016.
Information Disclosure Statement (IDS) Letter Regarding Common Patent Application(s), dated Jul. 1, 2015.
"International Search Report" and "Written Opinion of the International Searching Authority" (ISA/US) in Emtensor GmbH, International Patent Application Serial No. PCT/US2013/071360, dated May 27, 2014 (20 pages).
"International Search Report" and "Written Opinion of the International Searching Authority" (ISA/US) in Emtensor GmbH, International Patent Application Serial No. PCT/US2014/023803, dated Jun. 25, 2014 (9 pages).
"International Search Report" and "Written Opinion of the International Searching Authority" (ISA/US) in Emtensor GmbH, International Patent Application Serial No. PCT/US2014/023793, dated Oct. 31, 2014 (11 pages).
Yaniv, Ziv, et al. "Electromagnetic tracking in the clinical environment." Medical Physics, vol. 36, No. 3 (2009), pp. 876-892 (17 pages).
Fear, Elise C., et al. "Confocal microwave imaging for breast cancer detection: Localization of tumors in three dimensions." IEEE Transactions on Biomedical Engineering, vol. 49, No. 8 (2002), pp. 812-822 (11 pages).
"European Search Report" and "Written Opinion of the European Patent Office" in European Patent Application No. 11275103.7 for EMImaging Limited, dated Oct. 13, 2011 (5 pages).
Semenov, S. "Microwave tomography: review of the progress towards clinical applications." Philosphical Transactions of the Royal Society, vol. 367 (2009). pp. 3021-3042 (22 pages).
Semenov, S. Y., et al. "Development of microwave tomography for functional cardiac imaging." IEEE (2004), pp. 1351-1353 (3 pages).
"International Search Report" and "Written Opinion of the International Searching Authority" (ISA/US) in Emtensor GmbH, International Patent Application Serial No. PCT/US2017/063169, dated Jan. 30, 2018 (20 pages).
Information Disclosure Statement (IDS) Letter Regarding Common Patent Application(s), dated Feb. 3, 2017.
"Extended European Search Report," European Patent Application No. 14768372.6, for EMTensor GmbH, et al., dated Sep. 16, 2016 (10 pages).
"Extended European Search Report," European Patent Application No. 14768384.1, for EMTensor GmbH, et al., dated Oct. 20, 2016 (7 pages).
"Extended European Search Report," European Patent Application No. 13856581.7, for EMTensor GmbH, et al., dated Aug. 25, 2016 (7 pages).
"Extended European Search Report," European Patent Application No. 15193895.8, for EMTensor GmbH, dated May 25, 2016 (6 pages).
Semenov, S.Y., et al., "Myocardial Ischemia and Infarction Can Be Detected by Microwave Spectroscopy, 2. Biophysical Reconstruction," International Conference of the IEEE Engineering in Medicine and Biology Society (1996), pp. 1363-1364, vol. 4, published by IEEE (2 pages).
Jofre, L., et al., "Medical Imaging with a Microwave Tomographic Scanner," IEEE Transactions on Biomedical Engineering (Mar. 1990), pp. 303-312, vol. 37, No. 3 (10 pages).
Semenov, S.Y., et al., "Dielectrical Model of Cellular Structures in Radio Frequency and Microwave Spectrum, Electrically Interacting Versus Noninteracting Cells," Annals of Biomedical Engineering (2001), pp. 427-435, vol. 29, No. 5, published by Biomedical Engineering Society (9 pages).

(56) References Cited

OTHER PUBLICATIONS

Hawley, M.S., et al., "Microwave Imaging of Tissue Blood Content Changes," Journal of Biomedical Engineering (1991), pp. 197-202, vol. 13, No. 3, published by Butterworth-Heinermann for BES (6 pages).

Semenov, S., et al., "Microwave Tomography of Extremities: 1. Dedicated 2D System and Physiological Signatures," Physics in Medicine and Biology (2011), pp. 2005-2017, vol. 56, No. 7, published by Institute of Physics and Engineering in Medicine, United Kingdom (13 pages).

Information Disclosure Statement (IDS) Letter Regarding Common Patent Application(s), dated Mar. 9, 2016.

"International Preliminary Report on Patentability" of the International Bureau of WIPO in Emtensor GmbH, International Patent Application Serial No. PCT/US2013/071360, dated Jul. 7, 2015 (17 pages).

Zhu, Qingyou, Luo, CiYong, Zhong, ZhanLong, and Chen, Min You, "An Improved Back-Projection Algorithm for Electrical Impedance Tomography". Department of physic and electronic information Engineering, Yangtze Normal University, China. State Key Laboratory of Power Transmission Equipment & System Security and New Technology, Electrical Engineering of Chongqing University, China, (4 pages).

\* cited by examiner

METHODS OF ASSESSING THE NORMALCY OF BIOLOGICAL TISSUE

CROSS-REFERENCE TO RELATED APPLICATION

The present invention is a U.S. continuation patent application of, and claims priority under 35 U.S.C. § 120 to, U.S. nonprovisional patent application Ser. No. 13/894,401, filed May 14, 2013, which nonprovisional patent application published as U.S. Patent Application Publication no. 2014/0275944, and which application is a U.S. nonprovisional patent application of, and claims priority under 35 U.S.C. § 119(e) to, U.S. provisional patent application Ser. No. 61/802,339, filed Mar. 15, 2013, which provisional patent application is incorporated by reference herein.

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE PRESENT INVENTION

Field of the Present Invention

The present invention relates generally to electromagnetic field-based bio-sensing and bio-imaging, and in particular, to a handheld probe-based electromagnetic field technology that allows clinicians to assess functional and pathological conditions of biological tissue on-line at the point of care Background The successful management of a fractured bone involves an understanding of the two major components of any limb segment. These two components are the osseous or boney element and the soft tissue elements. Soft tissue elements are the skin, muscle, nerve and vessels while osseous element includes only the bone. The diagnosis and evaluation of the boney component is obvious to the treating physician by radiographic studies. The accurate assessment of the soft tissue component of the injured limb segment remains a major deficiency in management of fractures. To date several methods; such as laser Doppler and transcutaneous oxygen tensions have been attempted but they have been no better than clinical judgment. None of these methods have correlated with outcome. Consequently there is an important need to develop a simple effective method of assessing soft tissue viability.

It is important to understand soft tissue injury, as this component is often the determinant of the final outcome. The soft tissues provide the blood supply for the bone to heal, provide the coverage for the bone and the muscles, nerves and vessels provide for a functional outcome following injury. With the advent of higher energy trauma, more and more significant soft tissue disruption is being seen. The clinical problem exists with closed or open fractures as there is no method at the present to objectively evaluate soft tissue damage prior to surgical treatment. The surgical approach causes further damage to the soft tissues leading to necrosis, wound slough and infection. Consequently, surgeons require a method to accurately and objectively establish soft tissue viability so as to minimize the complication rate. In addition, associated injuries to the muscle such as a compartment syndrome and arterial disruption require soft tissue viability assessment to plan an appropriate management. A compartment syndrome occurs after an injury to an extremity when the obligatory muscle swelling becomes excessive. If the involved muscle is contained in an enclosed fascial space, this swelling will compromise arteriolar muscle blood flow leading to what has been called "a heart attack" of skeletal muscle. The issue of early diagnosis of compartment syndrome is very important, and is not limited to the management of fractures. The swollen limb without fracture is commonly seen and should be urgently assessed by orthopedic specialists. Undiagnosed compartment syndrome leads to muscle necrosis, contracture and irreversible neurological deficits. Extensive irreversible muscle damage can eventually result in sepsis or amputation. The incidence of complications is related to the speed in diagnosis and timing of fasciotomy. For this reason, delay of diagnosis and lack of aggressive surgical intervention has resulted in a high rate and amount of indemnity payment. In most patients, clinical examination is the most sensitive method of early diagnosis but in obtunded, head injured, or critically ill patients physical signs and symptoms are unreliable. Objective data is required in these situations and these measurements must be accurate and reproducible for diagnosis. Currently pressure measurements are the best means of determining need for fasciotomy but clinicians are unable to reach a consensus as to the critical pressure threshold. In addition, these tests are invasive, technique dependent, subjective and position sensitive.

Clinicians are always looking for simple non-invasive painless tests which provide the accurate clinical data necessary to make a rapid diagnosis. As to the monitoring of soft tissue viability in assessment of crush injuries, free muscle flap viability, arterial injury and reperfusion, at present there is not a consistent reliable instrument that is safe and non invasive. In this aspect, the concept of current invention is very appealing to the orthopaedic trauma surgeons as a method of non-invasive tissue viability assessment and monitoring. This technique would provide the surgeon with a measure of the soft tissue viability associated with a fracture. This would allow the treating surgeon to time surgical intervention appropriately, to avoid major disastrous complications and to be able to prognosticate the long-term functional outcome for patients. The invented technology combined with plain radiology in the acute emergency situation would provide the treating surgeon with a complete assessment of both components of any given injury. This would enhance drastically the ability of surgeons to provide quality and effective care for extremity injuries.

Various technologies making use of electromagnetic field phenomena in diagnosing, imaging, and treating various medical conditions. One of these technologies, electromagnetic tomography (EMT), is a relatively recent imaging modality with great potential for biomedical applications, including a non-invasive assessment of functional and pathological conditions of biological tissues. Using EMT, biological tissues are differentiated and, consequentially, can be imaged based on the differences in tissue dielectric properties. The dependence of tissue dielectric properties from its various functional and pathological conditions, such as blood and oxygen contents, ischemia and infarction malignancies has been demonstrated. Two-dimensional (2D), three-dimensional (3D) and even "four-dimensional" (4D) EMT systems and methods of image reconstruction have been developed over the last decade or more. Feasibility of the technology for various biomedical applications has been demonstrated, for example, for cardiac imaging and extremities imaging. Various patents and patent applications have discussed these technologies, including U.S. Pat. Nos. 5,715,819, 6,026,173, 6,332,087, 6,490,471, and 7,239,731, and U.S. patent application Ser. No. 13/173,078 (filed Jun. 30, 2011 and published on Jan. 12, 2012 as U.S. Patent Application Publication No. 2012/0010493 A1) and U.S. Patent Application Ser. No. 61/801,965 (filed Mar. 15, 2013) (a copy of the latter of which is attached hereto as Appendix A). The entirety of each of these patents and patent applications (and any publication of same) is incorporated herein by reference at least so far as such incorporation is consistent with the disclosure set forth herein.

Unfortunately, traditional EMT technologies, while producing very useful results, have required equipment that is physically cumbersome and difficult to use. This can be true both for the technician, diagnostician, or the like as well as the person or animal who is being studied. With regard to latter, the discomfort caused by the imaging chamber can also be significant. The size and weight of the equipment also makes it very difficult to use the equipment in the place where it is assembled; disassembling and moving the equipment is not very feasible. Finally, the use of arrays of antenna and other equipment creates significant complexity and cost. Thus, a need exists for technology that produces similar results but in a cheaper, more convenient, and more comfortable physical form. In particular a need exists for a more convenient, probe-based, hand-held technology that allows clinicians to assess functional and pathological conditions of biological tissue on-line at the point of care.

SUMMARY OF THE PRESENT INVENTION

Broadly defined, the present invention according to one aspect is a handheld electromagnetic field-based bio-sensing and bio-imaging system for use with a biological object, including: a handheld control unit; a handheld probe, connected to the control unit, that may be manipulated around a biological object while the probe irradiates an electromagnetic field, generated by the control unit, into the biological object and while the probe receives the irradiated electromagnetic field after being scattered and/or reflected by the biological object; and a tracking unit that tracks the position of the handheld probe.

In a feature of this aspect, the handheld probe is a first probe, and wherein the system further includes a second probe, connected to the control unit, that also irradiates an electromagnetic field. In a further feature, the second probe may manipulated around the biological object as it irradiates the electromagnetic field; the received electromagnetic field is analyzed in conjunction with other data to create an image, in at least two dimensions, of the biological object around which the probe is manipulated; the second probe is stationary relative to the biological object and to the first probe; and/or the second probe also receives an irradiated electromagnetic field, and wherein the second received electromagnetic field is also analyzed in conjunction with other data to create the image, in at least two dimensions, of the biological object around which the probes are manipulated.

In another feature of this aspect, the probe includes a waveguide. In further features, the waveguide is a ceramic waveguide; and/or the waveguide is a rectangular waveguide.

In another feature of this aspect, the probe includes a plurality of sensors whose positions are tracked by the tracking unit. In a further feature, the probe includes at least three sensors whose positions are tracked by the tracking unit.

In another feature of this aspect, an electromagnetic signal is generated by a Vector Network Analyzer and travels through a cable to a probe placed on the biological object where the electromagnetic signal is used to generate the electromagnetic field that is irradiated into the biological object.

In another feature of this aspect, the biological object is a human tissue. In a further feature, the received electromagnetic field is analyzed in conjunction with other data to create an image, in at least two dimensions, of the biological object around which the probe is manipulated.

In another feature of this aspect, the tracking unit may be external to the handheld control unit.

In another feature of this aspect, the tracking unit may be internal to the handheld control unit.

In another feature of this aspect, an electromagnetic signal is generated by a Vector Network Analyzer and travels through a cable to a first probe where the electromagnetic signal is used to generate the electromagnetic field that is irradiated into the biological object, and wherein the irradiated electromagnetic field is scattered and/or reflected by the biological object and received by a second probe. In further features, the scattered and/or reflected electromagnetic field is captured by an antenna device within the second probe and analyzed by the handheld control unit to determine functional and/or pathological conditions of the biological object; and/or the scattered and/or reflected electromagnetic field above is captured by an antenna device within the second probe and analyzed by the handheld control unit to determine if there is blood flow reduction.

In another feature of this aspect, the received electromagnetic field is analyzed in conjunction with other data to create an image, in at least two dimensions, of the biological object around which the probe is manipulated.

Broadly defined, the present invention according to another aspect is a method of assessing a functional and/or pathological condition of a biological tissue, including: generating, via a handheld control unit, an electromagnetic signal, the electromagnetic signal defining a first signal; communicating at least a portion of the first signal from the handheld control unit to a handheld probe via a wired connection; at the handheld probe, irradiating the first signal into the biological tissue; receiving the irradiated signal after the irradiated signal is scattered/reflected by the biological tissue, the received irradiated signal defining a second signal; combining at least a portion of the first signal with at least a portion of the second signal; and processing the combined portions of the first and second signals to assess the normalcy of the biological tissue.

In a feature of this aspect, the step of processing the combined first and second signals to assess the normalcy of the biological tissue is carried out at the handheld control unit.

In another feature of this aspect, the step of combining at least a portion of the first signal with at least a portion of the second signal is carried out by a Doppler sub-block. In further features, the step of combining at least a portion of the first signal with at least a portion of the second signal is carried out by a directional coupler within the Doppler sub-block; the directional coupler is a dual direction coupler; the directional coupler includes a first port, a second port, and a third port such that the first signal is received at the first port, at least a portion of the first signal is provided from the first port to, and output from, the second port, the second signal is received at the second port after being scattered/reflected by the biological tissue, and a portion of the second signal that is received at the second port is coupled with the portion of the first signal and output from the third port; and/or the directional coupler further includes a fourth port such that the portion of the first signal is a first portion, and a second portion of the first signal is output from the fourth port.

In another feature of this aspect, the method further includes a step of determining, via a tracking unit, the position of the handheld probe while the handheld probe is irradiating the first signal into the biological tissue.

In another feature of this aspect, the step of receiving the irradiated signal after the irradiated signal is scattered/reflected by the biological tissue is carried out at an antenna in the handheld probe.

In another feature of this aspect, the handheld probe is a first handheld probe, and wherein the step of receiving the irradiated signal after the irradiated signal is scattered/reflected by the biological tissue is carried out at a second handheld probe. In a further feature, the method further includes a step of determining, via a tracking unit, the position of the second handheld probe while the second handheld probe is receiving the irradiated signal after the irradiated signal is scattered/reflected by the biological tissue.

In another feature of this aspect, the step of combining at least a portion of the first signal with at least a portion of the second signal includes generating, via a directional coupler, a forward coupling path and a reverse coupling path. In further features, the step of combining at least a portion of the first signal with at least a portion of the second signal includes amplifying each of the forward coupling path and the reverse coupling path; the forward coupling path is connected to a first power splitter and the reverse coupling path is connected to a second power splitter; a first output of the first power splitter is connected to a first mixer, wherein a second output of the first power splitter is connected to a second mixer, wherein a first output of the second power splitter is connected to the first mixer, wherein a second output of the second power splitter is connected to the second mixer; an output of the first mixer is connected to a low pass filter, and an output of the second mixer is connected to a low pass filter; an output of the first mixer is connected to an analog-to-digital converter and an output of the second mixer is connected to an analog-to-digital converter; and/or processing the combined portions of the first and second signals to assess the normalcy of the biological tissue includes processing an output of the analog-to-digital converter.

Broadly defined, the present invention according to another aspect is a method of assessing status of a biological tissue, including: irradiating an electromagnetic signal, via a probe, into a biological tissue; receiving the irradiated electromagnetic signal after the signal is scattered/reflected by the biological tissue; providing blood flow information pertaining to the biological tissue; analyzing the received signal based at least upon the provided blood flow information and upon knowledge of electromagnetic signal differences in normal, suspicious, and abnormal tissue; using a dielectric properties reconstruction algorithm, reconstructing dielectric properties of the biological tissue based at least upon results of the analyzing step and upon blood flow information; and using a tissue properties reconstruction algorithm, reconstructing tissue properties of the biological tissue based at least in part upon results of the reconstructing step and upon blood flow information.

In a feature of this aspect, the method further includes a preliminary step of determining whether the probe is in the vicinity of the biological tissue. In further features, the method further includes a step of providing an indication, via the probe, as to whether the probe is determined to be in the vicinity of the biological tissue; the step of determining whether the probe is in the vicinity of the biological tissue is based at least in part upon knowledge of electromagnetic signal differences in biological tissue, air, and a gel; the method further includes a preliminary step of obtaining the knowledge of electromagnetic signal differences in biological tissue, air, and a gel via one or more physical/biophysical experiment; and/or the step of determining whether the probe is in the vicinity of the biological tissue includes determining whether the probe is in physical contact with the biological tissue.

In another feature of this aspect, receiving the irradiated electromagnetic signal includes receiving the irradiated electromagnetic signal at a probe. In further features, the probe via which the electromagnetic signal is irradiated is the same probe as the probe at which the irradiated electromagnetic signal is received; the probe via which the electromagnetic signal is irradiated is a different probe from the probe at which the irradiated electromagnetic signal is received; the method further includes a step of determining whether the probe at which the irradiated electromagnetic signal is received is in the vicinity of the biological tissue; the step of determining whether the probe at which the irradiated electromagnetic signal is received is in the vicinity of the biological tissue includes determining whether such probe is in physical contact with the biological tissue; the method further includes a step of determining, via a tracking unit, the position of the probe that receives the irradiated electromagnetic signal while the step of receiving is being carried out; the step of determining includes determining the position of a sensor disposed in the probe that receives the irradiated electromagnetic signal; the step of determining includes determining the position of at least three sensors disposed within the probe that receives the irradiated electromagnetic signal; the at least three sensors are spatially separated within the probe; the step of determining includes determining the position of the probe in three dimensions; the step of determining includes determining the position of the probe at multiple points in time; the method further includes a step of correlating the determined position of the probe to known information about the position and contours of the biological tissue; the method further includes a surfacing process, carried out prior to the step of receiving the irradiated electromagnetic signal, wherein the position of the probe, in at least two dimensions, is repeatedly determined as the probe is placed in different locations against the surface of the biological tissue, thereby developing a digital map of the surface of the biological tissue that is subsequently used in the correlating step; the reconstructed tissue properties are combined with the results of the correlating step to produce information regarding the status of the tissue relative to the geometry of the biological tissue; the method further includes a step of mapping the status of the tissue; the step of mapping the status of the tissue utilizes matching data from a database; the matching data in the database is based on previous experiments with animals and clinical studies with patients; and/or the method further includes a step of imaging the tissue based on the mapping step.

In another feature of this aspect, the blood flow information is provided at least partly on the basis of a step of synchronizing the received electromagnetic signal with a signal representing a blood circulation cycle of the biological tissue. In further features, the blood flow information is provided at least partly on the basis of a step, after the synchronizing step, of processing the synchronized signals using coherent averaging; and/or the step of providing the blood flow information includes providing blood volume information.

In another feature of this aspect, the irradiated electromagnetic signal is a first electromagnetic signal, wherein the received electromagnetic signal is a second electromagnetic signal and wherein the method further comprises a step of processing the first and second electromagnetic signals using a Doppler sub-block. In further features, the blood flow information is provided at least partly on the basis of a step of synchronizing an output of the Doppler sub-block with a signal representing a blood circulation cycle of the biological tissue; and/or the step of providing the blood flow information includes providing blood volume information.

In another feature of this aspect, the step of analyzing the received signal includes a preliminary step of obtaining the knowledge of electromagnetic signal differences in normal, suspicious, and abnormal tissue during clinical procedures. In a further feature, the step of obtaining the knowledge of electromagnetic signal differences in normal, suspicious, and abnormal tissue during clinical procedures includes correlating information about a particular electromagnetic signal with information from one or more tissue pathological study.

In another feature of this aspect, the step of reconstructing tissue properties of the biological tissue includes reconstructing cellular volume fraction ($VF_{cell}$).

In another feature of this aspect, the step of reconstructing tissue properties of the biological tissue includes reconstructing intracellular conductivity ($\sigma_{intracell}$).

In another feature of this aspect, the step of reconstructing tissue properties of the biological tissue includes reconstructing extracellular conductivity ($\sigma_{extracell}$).

In another feature of this aspect, the method further includes a step, after the step of reconstructing tissue properties of the biological tissue, of conducting visualization, imaging and matching analysis. In further features, the step of conducting visualization, imaging and matching analysis is based at least in part upon results of the step of reconstructing dielectric properties of the biological tissue; dielectric property information based on frequency is an input to the step of conducting visualization, imaging and matching analysis; dielectric property information based on time is an input to the step of conducting visualization, imaging and matching analysis; the step of conducting visualization, imaging and matching analysis is based at least in part upon results of the step of reconstructing tissue properties of the biological tissue; cellular volume fraction ($VF_{cell}$) is an input to the step of conducting visualization, imaging and matching analysis; intracellular conductivity ($\sigma_{intracell}$) is an input to the step of conducting visualization, imaging and matching analysis; extracellular conductivity ($\sigma_{extracell}$) is an input to the step of conducting visualization, imaging and matching analysis; the step of conducting visualization, imaging and matching analysis is based at least in part upon results of the step of analyzing the received signal; the step of conducting visualization, imaging and matching analysis is based at least in part upon results of the step of providing the blood flow information; the step of providing the blood flow information includes providing blood volume information; the step of providing the blood flow information includes providing blood velocity information; the step of providing the blood flow information includes providing blood direction information; and/or the blood flow information is provided at least partly on the basis of a step of synchronizing the received electromagnetic signal with a signal representing a blood circulation cycle of the biological tissue.

Broadly defined, the present invention according to another aspect is a method of imaging a biological tissue for identifying and locating tissue abnormalities, including: irradiating an electromagnetic signal, via a probe, in the vicinity of a biological tissue, the probe defining a transmitting probe; at a probe, receiving the irradiated electromagnetic signal after the signal is scattered/reflected by the biological tissue, the probe defining a receiving probe; providing blood flow information pertaining to the biological tissue; using a tissue properties reconstruction algorithm and blood flow information, reconstructing tissue properties of the biological tissue; determining, via a tracking unit, the position of at least one of the transmitting probe and the receiving probe while the step of receiving is being carried out, the at least one probe defining a tracked probe; and correlating the reconstructed tissue properties with the determined probe position so that tissue abnormalities can be identified and spatially located.

In a feature of this aspect, the transmitting probe is the same probe as the receiving probe.

In another feature of this aspect, the transmitting probe is a different probe from the receiving probe. In a further feature, the tracked probe includes both the transmitting probe and the receiving probe, all while the step of receiving is being carried out.

In another feature of this aspect, the method further includes a preliminary step of determining whether the tracked probe is in the vicinity of the biological tissue. In further features, the method further includes a step of providing an indication, via the tracked probe, as to whether the tracked probe is determined to be in the vicinity of the biological tissue; the step of determining whether the tracked probe is in the vicinity of the biological tissue is based at least in part upon knowledge of electromagnetic signal differences in biological tissue, air, and a gel; the method further includes a preliminary step of obtaining the knowledge of electromagnetic signal differences in biological tissue, air, and a gel via one or more physical/biophysical experiment; and/or the step of determining whether the tracked probe is in the vicinity of the biological tissue includes determining whether the tracked probe is in physical contact with the biological tissue.

In another feature of this aspect, the step of determining includes determining the position of a sensor disposed in the tracked probe. In further features, the step of determining includes determining the position of at least three sensors disposed within the tracked probe; and/or the at least three sensors are spatially separated within the tracked probe.

In another feature of this aspect, the step of determining includes determining the position of the tracked probe in three dimensions.

In another feature of this aspect, the step of determining includes determining the position of the tracked probe at multiple points in time.

In another feature of this aspect, the method further includes a step of correlating the determined position of the tracked probe to known information about the position and contours of the biological tissue. In further features, the method further includes a surfacing process, carried out prior to the step of receiving the irradiated electromagnetic signal, wherein the position of the tracked probe, in at least two dimensions, is repeatedly determined as the tracked probe is placed in different locations against the surface of the biological tissue, thereby developing a digital map of the surface of the biological tissue that is subsequently used in the step of correlating the determined position to position and contours of the biological tissue; the method further includes a step of mapping the status of the tissue; the step of mapping the status of the tissue utilizes matching data from a database; the matching data in the database is based on previous experiments with animals and clinical studies with patients; and/or the method further includes a step of imaging the tissue.

In another feature of this aspect, the blood flow information is provided at least partly on the basis of a step of synchronizing the received electromagnetic signal with a signal representing a blood circulation cycle of the biological tissue. In further features, the blood flow information is provided at least partly on the basis of a step, after the synchronizing step, of processing the synchronized signals using coherent averaging; and/or the step of providing the blood flow information includes providing blood volume information.

In another feature of this aspect, the method further includes a step of analyzing the received signal based at least upon the provided blood flow information and upon knowledge of electromagnetic signal differences in normal, suspicious, and abnormal tissue. In further features, the method further includes a step of using a dielectric properties reconstruction algorithm, reconstructing dielectric properties of the biological tissue based at least upon results of the analyzing step and upon blood flow information; the step of reconstructing tissue properties is based at least in part upon results of the step of reconstructing dielectric properties and upon blood flow information; the step of analyzing the received signal includes a preliminary step of obtaining the knowledge of electromagnetic signal differences in normal, suspicious, and abnormal tissue during clinical procedures; and/or the step of obtaining the knowledge of electromagnetic signal differences in normal, suspicious, and abnormal tissue during clinical procedures includes correlating information about a particular electromagnetic signal with information from one or more tissue pathological study.

In another feature of this aspect, the irradiated electromagnetic signal is a first electromagnetic signal, wherein the received electromagnetic signal is a second electromagnetic signal and wherein the method further comprises a step of processing the first and second electromagnetic signals using a Doppler sub-block. In further features, the blood flow information is provided at least partly on the basis of a step of synchronizing an output of the Doppler sub-block with a signal representing a blood circulation cycle of the biological tissue; the step of providing the blood flow information includes providing blood volume information; the step of providing the blood flow information includes providing blood velocity information; and/or the step of providing the blood flow information includes providing blood direction information.

In another feature of this aspect, the step of reconstructing tissue properties of the biological tissue includes reconstructing cellular volume fraction ($VF_{cell}$).

In another feature of this aspect, the step of reconstructing tissue properties of the biological tissue includes reconstructing intracellular conductivity ($\sigma_{intracell}$).

In another feature of this aspect, the step of reconstructing tissue properties of the biological tissue includes reconstructing extracellular conductivity ($\sigma_{extracell}$).

In another feature of this aspect, the step of correlating the reconstructed tissue properties with the determined probe position includes conducting visualization/imaging and matching analysis. In further features, dielectric property information based on frequency is an input to the step of conducting visualization/imaging and matching analysis; dielectric property information based on time is an input to the step of conducting visualization/imaging and matching analysis; cellular volume fraction ($VF_{cell}$) is an input to the step of conducting visualization/imaging and matching analysis; intracellular conductivity ($\sigma_{intracell}$) is an input to the step of conducting visualization/imaging and matching analysis; extracellular conductivity ($\sigma_{extracell}$) is an input to the step of conducting visualization/imaging and matching analysis; the step of conducting visualization/imaging and matching analysis is based at least in part upon results of a step of analyzing the received signal based at least upon the provided blood flow information and upon knowledge of electromagnetic signal differences in normal, suspicious, and abnormal tissue; the step of conducting visualization/imaging and matching analysis is based at least in part upon results of the step of providing the blood flow information; the step of providing the blood flow information includes providing blood volume information; the step of providing the blood flow information includes providing blood velocity information; the step of providing the blood flow information includes providing blood direction information; and/or the blood flow information is provided at least partly on the basis of a step of synchronizing the received electromagnetic signal with a signal representing a blood circulation cycle of the biological tissue.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

Further features, embodiments, and advantages of the present invention will become apparent from the following detailed description with reference to the drawings, wherein.

DETAILED DESCRIPTION

Figure 1:
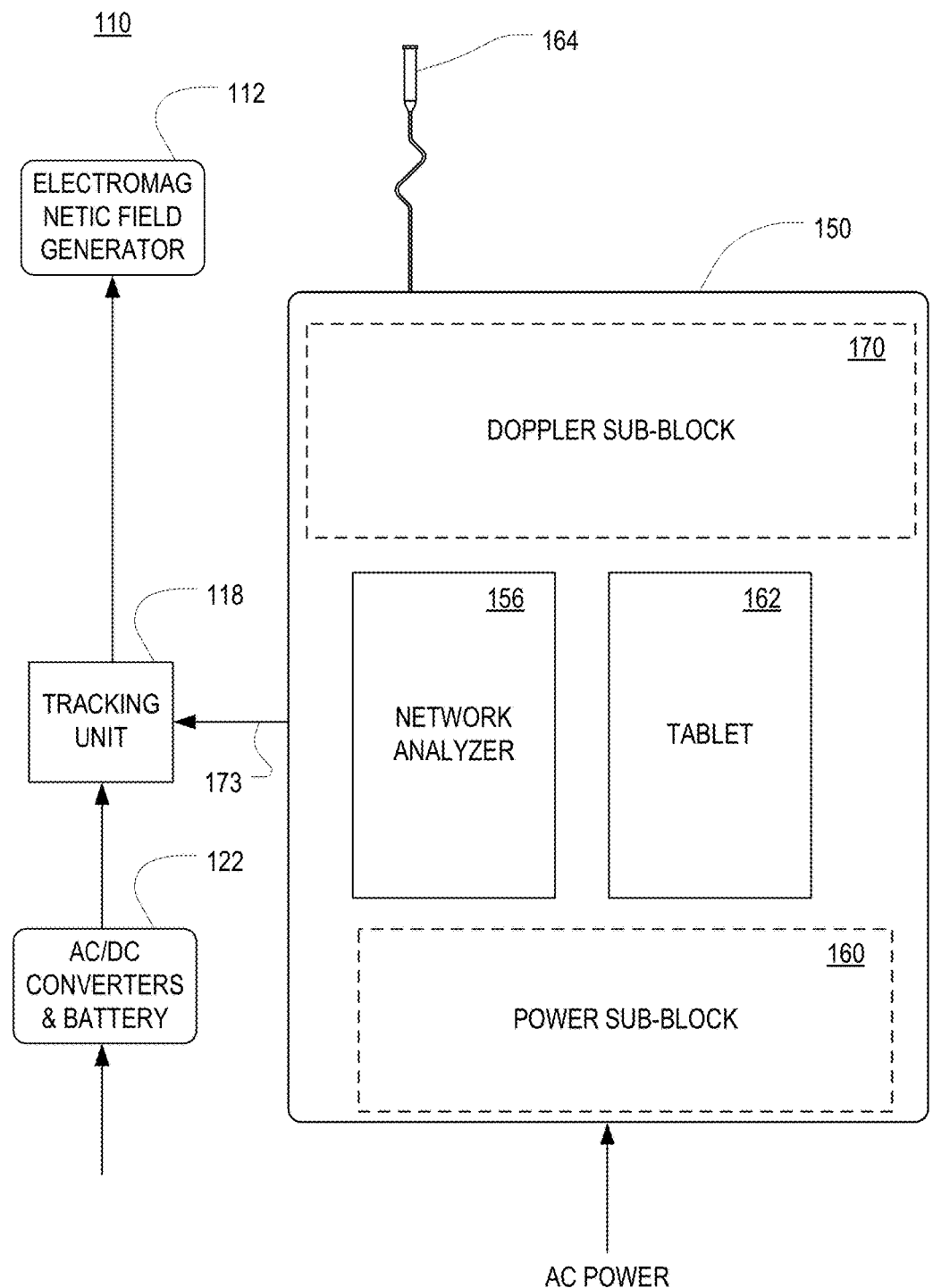
FIG. 1 is a block diagram of a handheld electromagnetic field-based bio-sensing and bio-imaging (EMFBioSI) system in accordance with a preferred embodiment of the present invention.

As a preliminary matter, it will readily be understood by one having ordinary skill in the relevant art ("Ordinary Artisan") that the present invention has broad utility and application. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. As should be understood, any embodiment may incorporate only one or a plurality of the above-disclosed aspects of the invention and may further incorporate only one or a plurality of the above-disclosed features. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Regarding applicability of 35 U.S.C. § 112, ¶6, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers," "a picnic basket having crackers without cheese," and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Referring now to the drawings, in which like numerals represent like components throughout the several views, the preferred embodiments of the present invention are next described. The following description of one or more preferred embodiment(s) is merely exemplary in nature and is in no way intended to limit the invention, its application, or uses.

FIG. 1 is a block diagram of a handheld electromagnetic field-based bio-sensing and bio-imaging (EMFBioSI) system 110 in accordance with a preferred embodiment of the present invention. The system 110 includes a handheld control unit 150, a handheld probe 164, an external electromagnetic field generator 112, and an external tracking unit 118. A power supply 122, which may include an AC/DC converter and one or more batteries, may be provided for the tracking unit 118.

Figure 2:
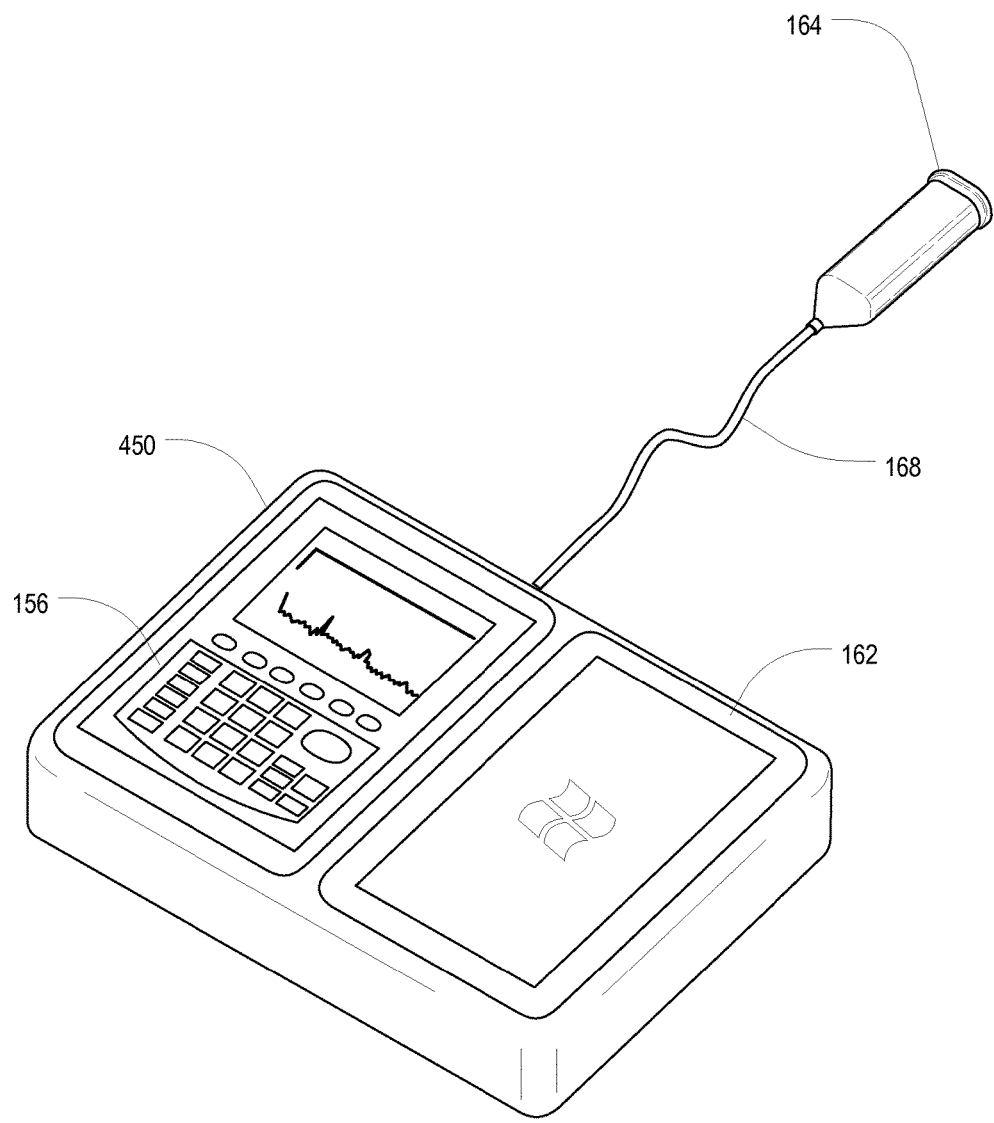
FIG. 2 is a perspective view of one possible implementation of the handheld control unit and probe of the system of FIG. 1.
Figure 3:
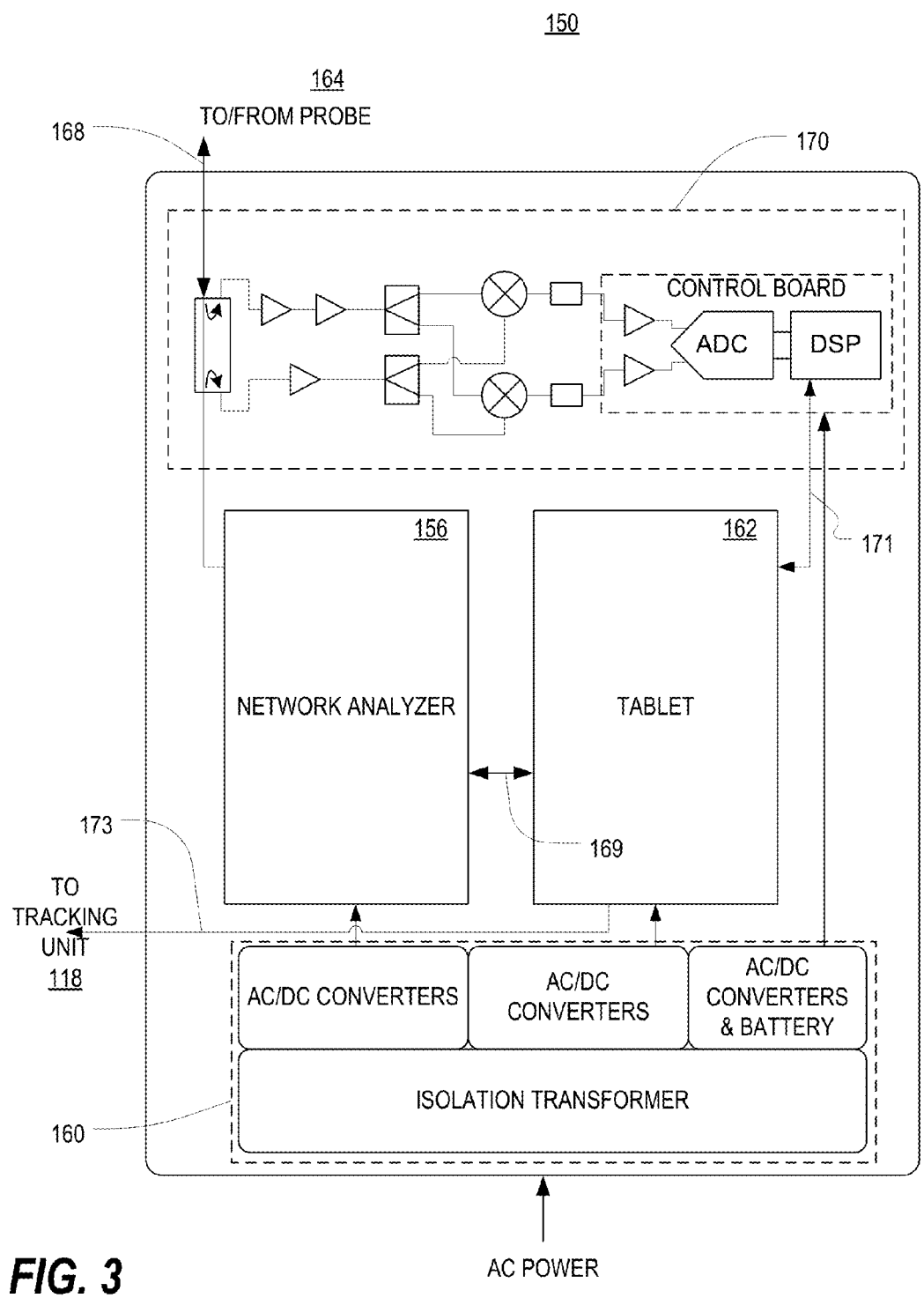
FIG. 3 is a block diagram of the handheld control unit of the system of FIG. 1.

FIG. 2 is a perspective view of the handheld control unit 150 and probe 164 of the EMFBioSI system 110, and FIG. 3 is a block diagram of the control unit 150 of FIG. 1. Notably, unlike prior art systems, the control unit 150 is not physically cumbersome. The control unit 150 includes a Doppler sub-block 170, a portable Vector Network Analyzer (VNA) (for example, Agilent FieldFox 2ports portable VNA) 156, a tablet computer 162, and a power sub-block 160. The tablet computer 162 provides primary control, including a primary user interface, to a user. The tablet computer 162 is communicatively connected to the VNA 156, which generates EM signals having desired parameters, via a first communication link 169, and is likewise communicatively connected to the Doppler sub-block 170, which processes received signals after they have passed through an interrogation region, via a second communication link 171. The tablet computer 162 is also communicatively connected to the external tracking unit 118 via a third communication link 173.

EM signals generated by the VNA 156 pass through the cable to the probe 164 and interrogate the tissue via irradiation. The EM signal reflected by or transmitted through the tissue passes back to VNA 156 through the probe and coaxial cable to the same port (or a second port, as described later) and the complex reflected or transmitted EM signal is measured by VNA, for example in form of amplitude and phase or in form of real and imaginary parts of the signal. Traditionally, the EM signal irradiated from the first port, reflected by the sample and measured by the same first port is called $S_{11}$. (Similarly, when a second probe is utilized as described later, an EM signal irradiated from the second port, reflected by the sample and measured by the first port is called $S_{21}$.) The overall signal generated by port i and measured in port j after being affected by the sample is called $S_{ij}$. All of this is further discussed elsewhere herein.

As further described hereinbelow, controlled EM signals generated by the VNA 156 are also provided to the Doppler sub-block 170 by a fourth communication link 152. The EM signal travels via a probe connection 168 to the probe 164. In at least some embodiments, the probe connection 168 utilizes a high quality coaxial cable 168. As also described below, the probe 164 both delivers the EM signals and receives them after they pass through or are reflected by the interrogation region. After being received by the VNA, they are processed by the Doppler sub-block 170, with the output being processed by an application on the tablet computer 162.

Figure 4:
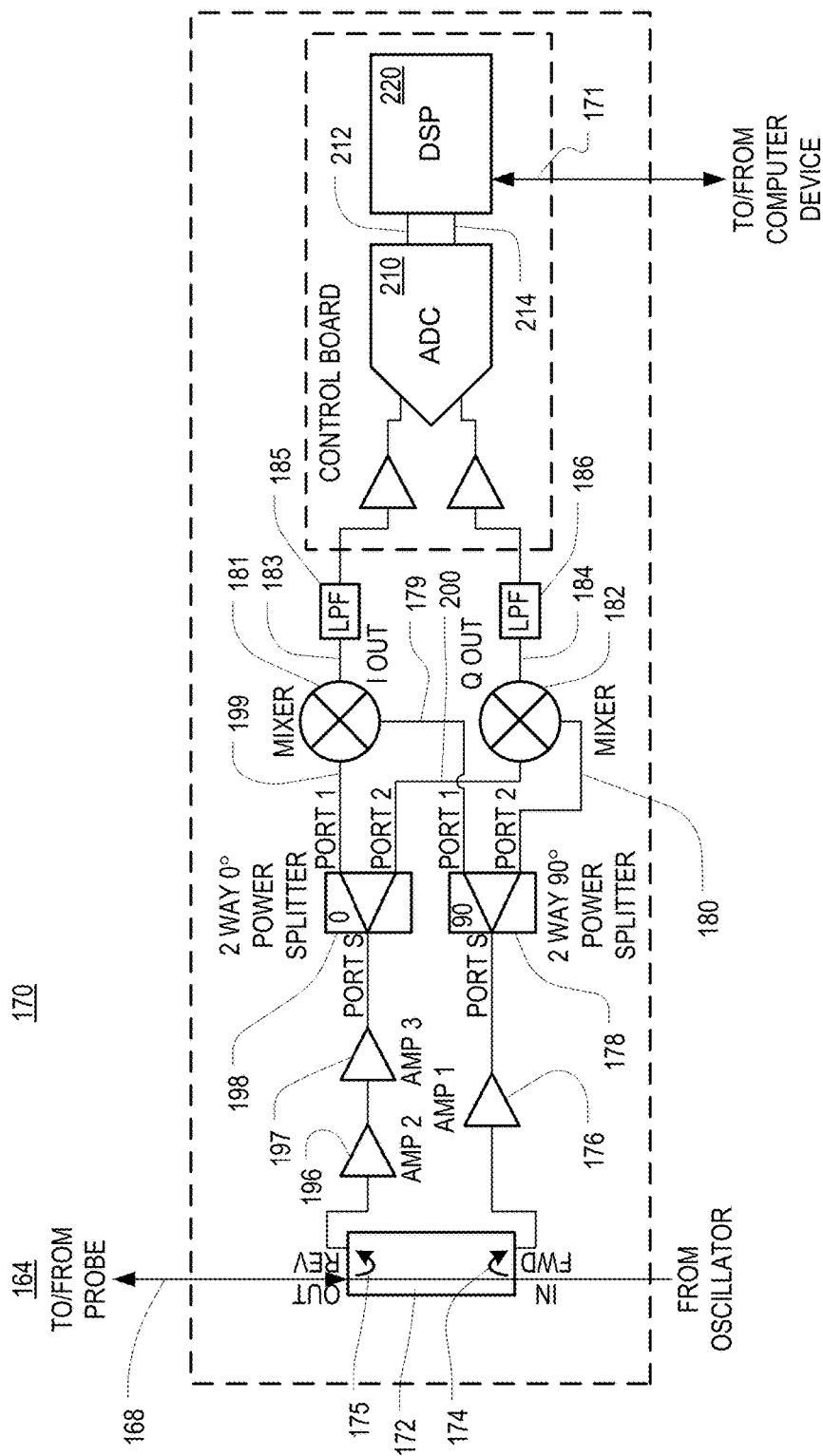
FIG. 4 is a block diagram of the Doppler sub-block used in the system of FIG. 1.

FIG. 4 is a block diagram of the Doppler sub-block 170 used in the system 110. The Doppler sub-block 170 includes a dual direction coupler 172 having a forward coupling path 174 and a reverse coupling path 175. The output of the forward coupling path 174 is connected to a first amplifier 176, whose output is connected to a two-way 90° power splitter 178. The output of the reverse coupling path 175 is connected to a second amplifier 196 and then a third amplifier 197, whose output is connected to a two-way 0° power splitter 198. The outputs 179,180,199,200 of the power splitters 178,198 are connected to mixers 181,182 whose outputs 183,184 are connected to low pass filters 185,186. One device suitable for use as the mixers 181,182 is a Mini-Circuits ZFM. The output of each low pass filter 185,186 is connected to a respective amplifier and then to an analog-to-digital converter (ADC) 210, and the outputs 212,214 of the ADC 210 are connected to a digital signal processor 220.

In operation, the EM signal from the VNA 156 is directed to the probe 164 through a dual direction coupler 172. The same EM signal passes through a forward coupling path 174, goes through an amplifier 176, and then passes through a two-way 90° power splitter 178 to obtain an in-phase signal on one output 179 and a quadrature phase signal on its other output 180. In at least one embodiment, the EM signal from the VNA 156 is provided at a level of 0 dBm (0.001 W), the EM signal passing through the forward coupling path 174 is with power of −20 dBm (0.01 mW), and the resulting signal is amplified by 30 dB to +10 dBm (10 mW).

Figure 5:
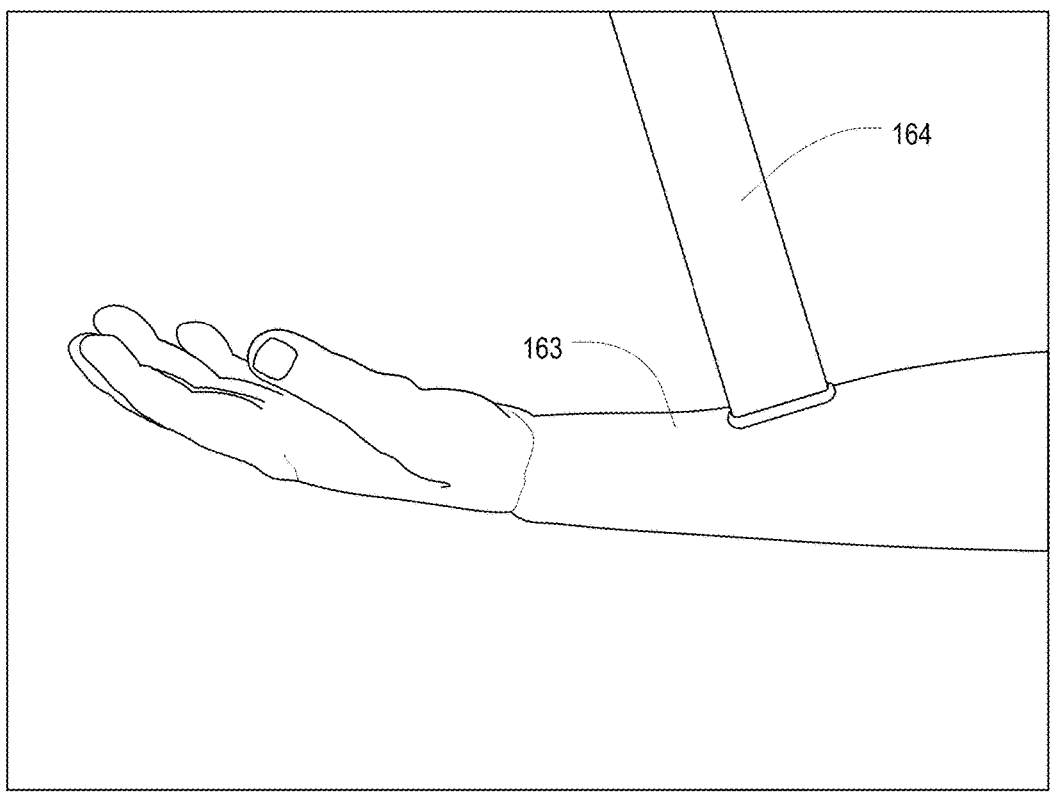
FIG. 5 is a perspective view of the probe of FIG. 2, being placed on a human arm.

Meanwhile, the main EM signal from the VNA 156 is directed to the probe 164 for interrogation of a biological object 163 in the interrogation region. FIG. 5 is a perspective view of the probe 164, of FIG. 1 used in the EMFBioSI system 110, being placed on a human arm 163. The EM signal 152 from the VNA 156 is received directly by the probe 164 through the coaxial cable 168. The probe 164 sends the signal into the tissue of the arm 163. A resulting signal is reflected and scattered by the tissue of the arm 163 back to the probe 164, where it is received and sent back to the control unit 150 via the coaxial cable 168.

Although only a single probe is utilized in the embodiment described thus far, it will be appreciated that one or more additional probes could be utilized. In such an arrangement, a signal received by one probe could have been transmitted by the same probe, or by a different probe. Thus, each received signal is sometimes referred to hereinafter as $S_{jk}$, where the index j refers to the jth port of VNA 156, which has a probe connected to the port. The jth port generates the original electromagnetic signal and transmits it to a probe toward the interrogation zone. The index k refers to the kth port of the VNA 156 which in some embodiments has a probe connected to the port. The kth port via an antenna in the probe, receives or collects the reflected/scattered EM signal. In the EMFBioSI system 110 described thus far, exactly one probe 164 exists, and therefore j=1, k=1, and the signal received back at the control unit 150 is designated $S_{11}$. Other embodiments may utilize more than one probe. For example, in an embodiment described hereinbelow, two probes are utilized. In various two-probe embodiments, other received signals may, for example, be designated as $S_{22}$, $S_{21}$, and $S_{12}$.

Referring again to FIG. 4, part of a reflected EM signal or field passes through the probe 164 and the cable into the dual direction coupler 172 where it is directed through the reverse coupling path 175. The output is passed through two amplifiers 196,197 and then through a two-way 0° power splitter 198 to obtain an in-phase signal on one output 199 and a quadrature phase signal on its other output 200. In at least one exemplary embodiment, the reflected EM signal is received at the dual direction coupler 172 with power −50 dBm, and is amplified by 60 dB and then +10 dBm by the two amplifiers 196,197.

The four signals carried by the respective outputs 179, 180,199,200 from the power splitters 178,198 are now combined for analysis. The in-phase signal on the first output 179 of the two-way 90° power splitter 178, whose original source was the VNA 156, and the signal on the first output 199 of the two-way 0° power splitter 198, whose original source was the EM signal reflected and scattered by the tissue, are sent through a first mixer 181 (Mini-Circuits ZFM-2000) to produce an in-phase signal I_out at its output 183. Meanwhile, the quadrature signal on the second output 180 of the two-way 90° power splitter 178, whose original source was the VNA 156, and the signal on the second output 200 of the two-way 0° power splitter 198, whose original source was the EM signal reflected and scattered by the tissue, are sent through a second mixer 182 and produce a quadrature signal Q_out at its output 184. Then I-Out and Q-Out are each routed through a respective low pass filter 185,186 and into the ADC 210, and the digitized signals on the ADC outputs 212,214 are provided to the DSP 220 or directly to a computer 162 for further signal analysis and processing.

Figure 6A:
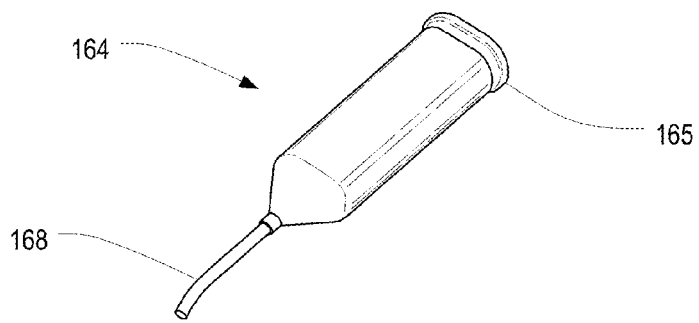
FIG. 6A is a perspective view of the probe of FIG. 2.
Figure 6B:
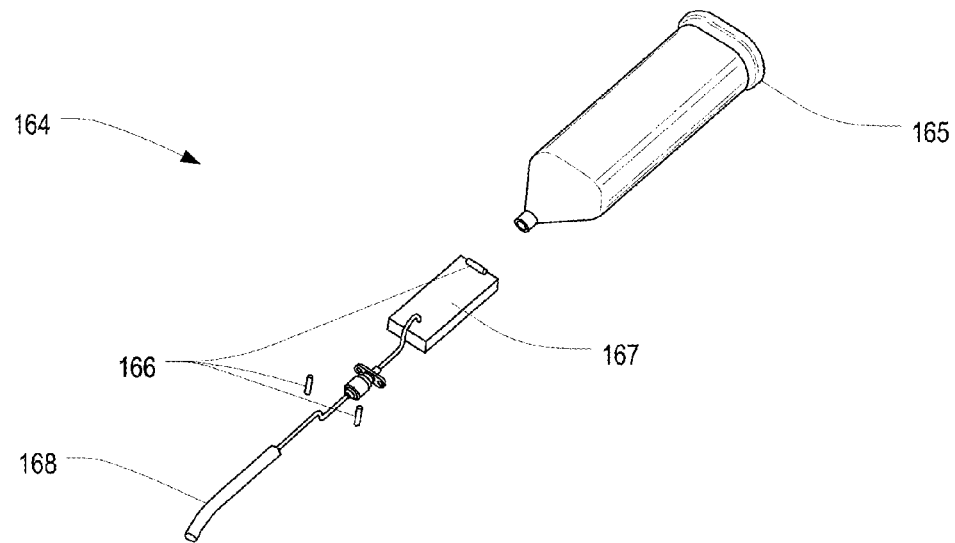
FIG. 6B is an exploded perspective view of the probe of FIG. 2, showing three position tracking sensors and a rectangular waveguide.

FIG. 6A is a perspective view of the probe 164 of FIG. 1. FIG. 6B is an exploded perspective view of the probe of FIG. 6A, showing three position tracking sensors 166 and a waveguide 167. In at least one embodiment, the waveguide is a rectangular waveguide. The spatial positions (x(t),y(t), z(t)) of each of the position tracking sensors 166 over time are tracked by the tracking unit 118. A suitable example of such a unit is the Aurora system by NDI, available at http://www.ndigital.com/medical. Notably, although the probe 164 illustrated and described herein includes three sensors 166, it will be appreciated that other embodiments may use more than three sensors. The three position tracking sensors 166 are spatially separated within the probe 164 to allow for tracking the position (x(t),y(t),z(t)) of the probe head 165 during clinical study in relation to the surface of biological tissue 163. The position tracking sensors 166 are also used to track the angle at which the EM signal irradiated from the probe 164 interrogates the tissue. The information from these sensors 166 is needed in order to provide two-dimensional tissue surface mapping/imaging, as the signal location and angle should be known for both surfacing and proper image reconstruction.

The core of the probe 164 includes a waveguide 167. In some embodiments, a waveguide might be rectangular. In some embodiments, the rectangular waveguide 167 is filled with a matching material that may be selected or designed such that its dielectric properties match the dielectric properties of biological tissues and to minimize the dimensions of the probe 164. In this regard, the dielectric properties of biological tissues are well known and tabulated. For example, at 1 GHz they vary from $\varepsilon=55+j23$ for tissues with high water content (muscle, skin) to $\varepsilon=5+j1.5$ for tissues with low water content (fat, bone). One example of a suitable matching material is a ceramic with $\varepsilon \sim 60$ and low attenuation, and one suitable ceramic waveguide 167 may thus be constructed having dimensions of, for example, 21×7.5×53 mm, which result in corresponding probe dimensions that are within a clinically acceptable range. Useful dielectric property information may be found in Gabriel S, Lau R W and Gabriel G 1996, "The dielectric properties of biological tissues: II. Measurements in the frequency range 10 Hz to 20 GHz," *Phys. Med. Biol.* 41 2251-69 ("Gabriel"), the entirety of which is incorporated herein by reference.

For rectangular waveguides with A>B (for example, where A=21 mm and B=7.5 mm), where A and B are the side dimensions of the waveguide, the lowest critical (cutoff) frequency is in dominant $H_{10}$ mode. The frequency is determined by:

$$f_{1,0} = 1/2A\sqrt{\mu\varepsilon} \tag{1}$$

where:
A—size [m] of largest side of the waveguide on cross-section B×C;
f—frequency [Hz];
$\mu=\mu^*\mu_0$ where $\mu_0$—permeability of vacuum and $\mu$—relative permeability (=1 in our conventional case);
$\varepsilon=\varepsilon^*\varepsilon_0$ where $\varepsilon_0$—permittivity of vacuum and $\varepsilon$—relative permittivity (=60 in our conventional case). Equation (1) may be simplified for SI units. Then, using:

$$c = 1/\sqrt{\mu_0 \varepsilon_0} \tag{2}$$

where:
c—speed of light in vacuum=2,9979*10$^8$ [m/sec]
the following is obtained:

$$f_{1,0} = c/2A\sqrt{\mu\varepsilon} \tag{3}$$

where $\varepsilon,\mu$ are relative complex permittivity and permeability of the waveguide material. For example, in a conventional case and in an exemplary rectangular waveguide with dimensions provided above, and assuming that the real portions of both $\varepsilon,\mu$ are higher than their imaginary parts:

$$f_{1,0} = c/2A\sqrt{\mu\varepsilon} = 0.29979/(2*0.021*\sqrt{60})[GHz] = 0.921[GHz] \tag{4}$$

Complete details on the above equations (1)-(4) are provided in J. D. Jackson "Classical Electrodynamics", 3$^{rd}$ edition, John Wiley & Sons, Inc, 1999, the entirety of which is incorporated herein by reference.

Because the permeability of the majority of biological tissue is equal to 1, by using a "special material" with permittivity within a region of 30-60 and with permeability of more than 1, it is possible to still maintain a good EM match and to decrease the size of the probe 164, allowing the preferred embodiment to contain a multi-head (multi-waveguide) probe. Suitable ceramic waveguides may be made using a conventional three step manufacturing process. In a first step, a ceramic plate (in our exemplary case, with dimensions 53×21×7.5 mm with desired hole) is made. This may be done using a proper furnace or the like to sinter a powder of so called parent compounds. An example of a parent compound is a barium titanate ($BaTi_4O_9$ or $Ba_2Ti_9O_{20}$). The second step is the metallization of all surface of the ceramic plate except the one that is an EM irradiation surface and excitation hole. This might be done by applying a highly conductive (usually silver) paste and then heating. The third step is to connect the outer conductor of coaxial cable with one metallized surface and inner conductor with the opposite metallized surface through an excitation hole. The increased permeability of an EM waveguide is achieved at the first step of the manufacturing by mixing a powder of conventional parent compound (for example, a barium titanate ($BaTi_4O_9$ or $Ba_2Ti_9O_{20}$)) with a powder of magnetic materials of high permeability and small losses at microwave frequencies. Conventional ferrites (for example, NiZn or MnZn) have shown high permeability at low (kHz) frequencies but exhibit significant decrease in permeability and increase in losses at high (MHz-GHz) frequencies. The frequencies of our interest are near 1 GHz. This frequency region is of great interest for various industrial applications of materials with high magnetic permeability, for example wireless communications and data storage. In our case, potential useful magnetic materials might include 1) nanocrystaline Fe—Co—Ni—B based material with effective magnetic permeability of about 500-600 at 1 GHz region[4], Co—Fe—Zr—B or Co—Fe—Si—B; and/or 2) novel hexa-ferrites (with formula $M(Fe_{12}O_{19})$, where M is usually barium Ba, strontium, Calcium Ca or Lead Pb) with complex permittivity and permeability that can vary with composition of materials and frequency.

Technology Algorithms and Work Flow

Figure 7:
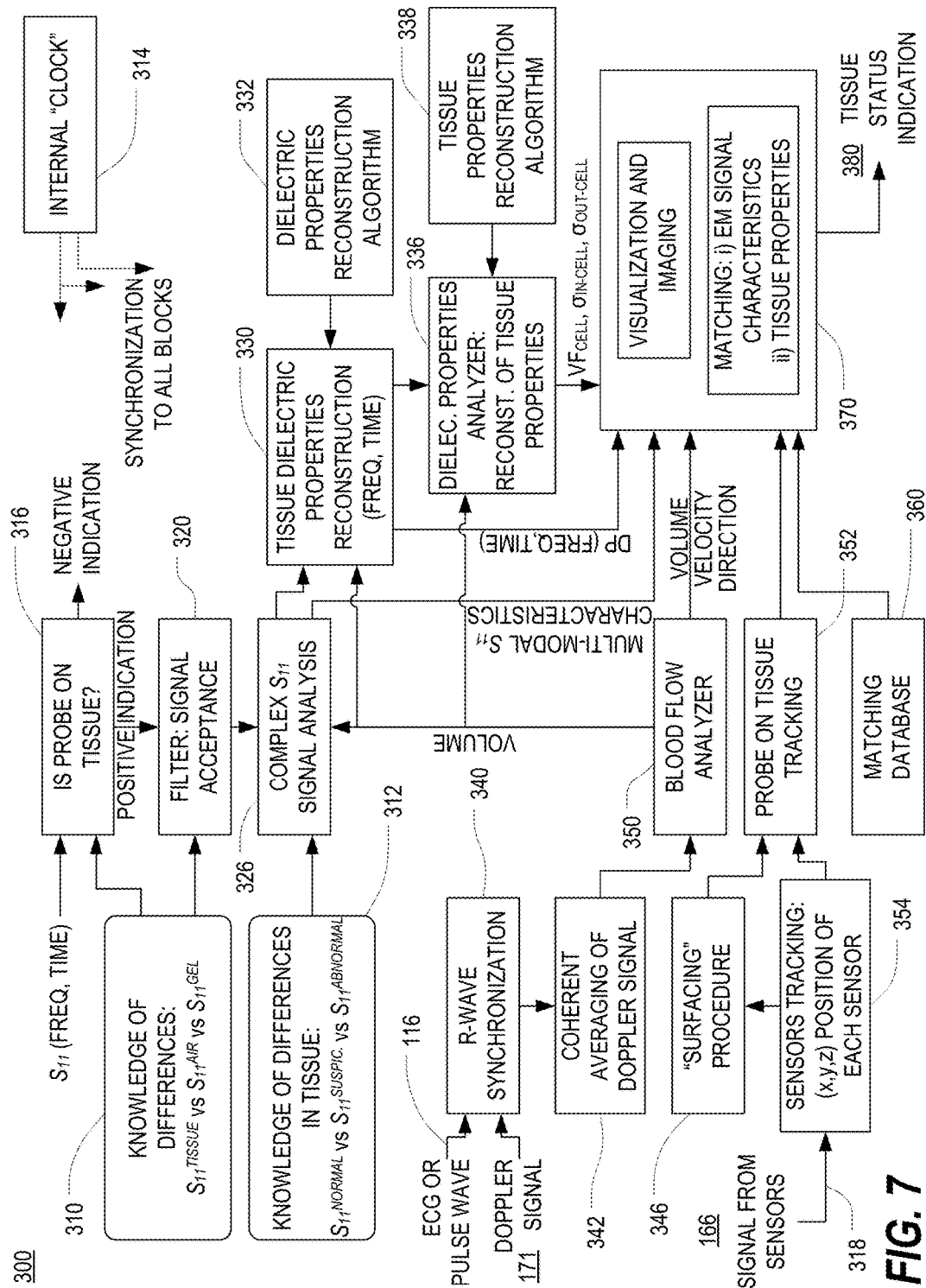
FIG. 7 is a flow diagram of the operational process of the EMFBioSI system of FIG. 1 in accordance with one or more preferred embodiments of the present invention.

FIG. 7 is a flow diagram of the operational process 300 of the EMFBioSI system 110 of FIG. 1 in accordance with one or more preferred embodiments of the present invention. As shown therein, this process 300 utilizes a number of input signals, including $S_{11}$, introduced in FIG. 4; an internal clock 314; the output of the Doppler sub-block 170, introduced in FIG. 4; sensor signals 318, and an electrocardiography (ECG) or plethysmography signal 116. The process 300 also utilizes additional data and other information, obtained or derived prior to operation and stored in a database or elsewhere in the system 110. Such information, which serves as control data, includes material type information (control data) 310 pertaining to the how the characteristics of $S_{11}$ vary based on whether $S_{11}$ passes through tissue, air, or a gel, and tissue status information (control data) 312 pertaining to "normal," "suspicious," and "abnormal" characteristics of $S_{11}$. Such material type information or control data 310 may be obtained via physical/biophysical experiments, while the tissue status information or control data 312 may be obtained during previous clinical procedures when a particular EM signal $S_{11}$ is correlated with tissue pathological studies.

The material type control data 310 is used in a decision block 316 where it is determined whether the probe 164 is on biologic tissue 163 or not. In order to facilitate ease of use by the operator, an indication of whether the probe 164 is properly on the tissue 163 or not. Such an indication might include a green light, a beep, or the like. A corresponding indication when the probe 164 is not on the tissue, such as a red light, a buzzer, or the like, may also be provided. The material type control data 310 is also provided as an input to a filter 320. Once it is determined the probe is on tissue 163 and the signal is within a valid range to pass the filter 320, the signal is ready for complex $S_{11}$ signal analysis at block 326.

This block 326 also requires input from the tissue status control data 312 and a blood flow analyzer 350. The tissue status control data, which corresponds to the differences in the value of $S_{11}$ resulting from normal, suspicious, or abnormal tissue, is stored in a computer database and is compared on-line with a received EM signal $S_{11}$. Correlation and cross-correlation analysis as well as pattern recognition methods may be used.

The blood flow analyzer 350 is based on the use of a Doppler signal that has been processed using R-wave synchronization at block 340 and coherent averaging at block 342. This is explained as follows. A signal at Doppler frequency is small and comparable to noise. At block 342, a coherent averaging process is used to detect a signal with amplitude, which is comparable or less than the amplitude of noise. Assume N realizations of similar signals x(t) with its jth realization in the form:

$$y_j(t) = x(t) + \text{noise}(t)$$

where x(t) is the signal and noise(t) is random noise, the averaging over N realizations yields:

$$y = \frac{1}{N}\sum_{j=1}^{N} y_j(t) = \frac{1}{N} Nx(t) + \frac{1}{N}\sum_{j=1}^{N} \text{noise}(t) = x(t) + \frac{1}{N}\sum_{j=1}^{N} \text{noise}(t)$$

The amplitude of random noise is decreased by a factor of N. The condition of coherent signals is achieved in at least some embodiments of the system 110 through synchronization 340, sometimes referred to herein as R-Wave synchronization (based on use of the "R" component of the QRS complex seen in a typical electrocardiogram), of the realizations of the Doppler signal 171 and blood circulation cycles as represented by electrocardiography (ECG) or plethysmography input signal 116. The received Doppler signals 171, coherently averaged with respect to the circulation cycle, are signals x(t) in the above equation example. Coherent averaging is possible as a result of the synchronization with the circulatory cycles (R-wave synchronization) that are provided by independently measured ECG or R-pulses or plethysmography, or by other means of synchronization with circulatory activity.

Returning to FIG. 7, the complex $S_{11}$ signal analysis is now performed at block 326 using the input from the tissue status control data 312, the filter 320, and the blood flow analyzer 350. By changing the excitation frequency (higher than the dominant mode), different Transverse Electric (TE) and Transverse Magnetic (TM) modes will be excited. This also will change the polarization of the irradiated EM field. By looking at different multi-modal $S_{11}$ it would be possible to assess tissue types and functional conditions of a particular tissue being studied. Blood flow volume information, received from "Blood flow analyzer" block 350, is used in the "Complex $S_{11}$ Signal Analysis" 326 to assess the tissue related changes in $S_{11}$. In particular, the frequency shift of the received Doppler signal 171 is proportional to the velocity/direction of the arterial blood flow, and the strength (or amplitude) of the signal is proportional to the volume of the flowing arterial blood.

When the complex $S_{11}$ signal analysis 326 is completed, tissue dielectric properties reconstruction is performed at block 330. This reconstruction utilizes the measured EM signal $S_{11}$ information and results of the complex $S_{11}$ signal analysis 326, output from block 326; information about the volume of blood received from the blood flow analyzer 350; and a dielectric properties reconstruction algorithm 332. Blood volume with tabulated dielectric properties, discussed in the Gabriel reference, is taken into account when assessing a tissue volume and its dielectric properties using multi-component dielectric mixture theory. See Landau L. D. and E. M. Lifshitz, Electrodynamics of Continuous Media, $2^{nd}$ edition, Pergamon Press, Oxford, 1984 ("Landau") for details on multi-component dielectric mixture theory. One example of a suitable dielectric property reconstruction algorithm is found in Bois K J, Benally A D and R Zoughi "Multimode solution for the reflection properties of an open-ended rectangular waveguide radiating into a dielectric half-space: the forward and inverse problems," IEEE Trans IM, 1999, 48, 6, 1131-1140.

After the tissue dielectric properties are reconstructed in block 330, tissue properties, such as cellular volume fraction ($VF_{cell}$), intracellular conductivity ($\sigma_{intracell}$), and extracellular conductivity ($\sigma_{extracell}$), are reconstructed in the dielectric properties analyzer 336. The tissue property reconstruction carried out by the dielectric properties analyzer 336 utilizes the bulk dielectric properties of tissue over frequency and time, obtained from tissue dielectric properties reconstruction at block 330; information received from the blood flow analyzer 350 about the volume of blood; and a tissue properties reconstruction algorithm 338. Again, blood volume with tabulated dielectric properties is taken into account when assessing a tissue volume and its dielectric properties using multi-component dielectric mixture theory. Examples of suitable tissue properties reconstruction algorithms are found in Semenov S. Y., Simonova G. I., Starostin A. N., Taran M. G., Souvorov A. E., Bulyshev A. E., Svenson R. H., Nazarov A. G., Sizov Y. E., Posukh V. G., Pavlovsky A., Tatsis G. P., "Modeling of dielectrical properties of cellular structures in the radiofrequency and microwave spectrum/Electrically interacting vs non-interacting cells," *Annals of Biomedical Engineering*, 2001, 29, 5, 427-435, and in Semenov S. Y., Svenson R. H., Bulyshev A. E., Souvorov A. E., Nazarov A. G., Sizov Y. E., Posukh V. G., Pavlovsky A., Tatsis G. P., "Microwave spectroscopy of myocardial ischemia and infarction/2. Biophysical reconstruction," *Annals of Biomedical Engineering*, 2000, 28, 1, 55-60. The entirety of each of these references is incorporated herein by reference.

During operation of the system 110, it may be necessary or useful to identify a biological area of interest as a 3D surface in order to make space-time correlations between the actual position of the diagnostic probe at a particular time of the procedure and particular portions of a biological sample under the study. In at least some embodiments, this is achieved using a "surfacing" procedure 346 that is conducted during an initial phase of the clinical study of a biological area of interest. An operator may move the probe 164 in various ways along an area of assumed clinical interest while position determinations are conducted. For example, an operator may first move the probe along the assumed boundary of an area of clinical interest and second move the probe along two non-parallel lines inside an area of assumed clinical interest. Other movement patterns are likewise possible, such as by making continual lines or by placing the probe at different points.

In some situations, such as in the case when movement in an area of clinical interest is anticipated during a diagnostic procedure, it may be useful to conduct the surfacing procedure 346 on-line during the diagnostic procedure. In this particular case, multiple position tracking sensors 166 may be physically attached directly to biological tissue in a similar manner, for example, the way that disposable ECG electrodes are conventionally attached to biological tissue.

During the surfacing procedure 346, the positions of the sensors 166 are tracked or determined in three dimensions in the sensor tracking block 354 and analyzed so that the location and contours of the surface of biological tissue of clinical interest are known in two, or preferably three, dimensions and supplied in digital form into the "probe on tissue tracking" block 352. In this block 352, the positions of the sensors 166 continue to be tracked and compared to the known data regarding the surface of the tissue itself 163 so as to determine the position of the probe 164 on the tissue 163.

The operational process 300 culminates at block 370 with visualization of the position of the probe on the object under study, imaging of dielectric and other properties (such as those described below and/or elsewhere herein) of the tissue, and matching analysis. Here, multi-modal $S_{11}$ characteristics (such as frequency, amplitude, and phase of $S_{11}$ signal, and polarization of E-field for each mode) from the complex $S_{11}$ signal analysis at block 326, dielectric property information based on frequency and time from the tissue dielectric properties reconstruction at block 330, tissue property information (such as $VF_{cell}$, $\sigma_{intracell}$, and $\sigma_{extracell}$) from the dielectric properties analyzer 336, blood flow information such as volume, velocity, and direction of blood flow from the blood flow analyzer 350, probe position information from the probe/tissue position tracker 352, and matching data from a matching database 360 are utilized to provide visualization of the probe position on the object under study and imaging of dielectric properties of the tissue 163, and to match characteristics of the EM signal $S_{11}$ to tissue properties in order to provide an indication 380 of tissue status to the operator. The matching database 360 contains data based on previous experiments with animals and clinical studies with patients.

Figure 8:
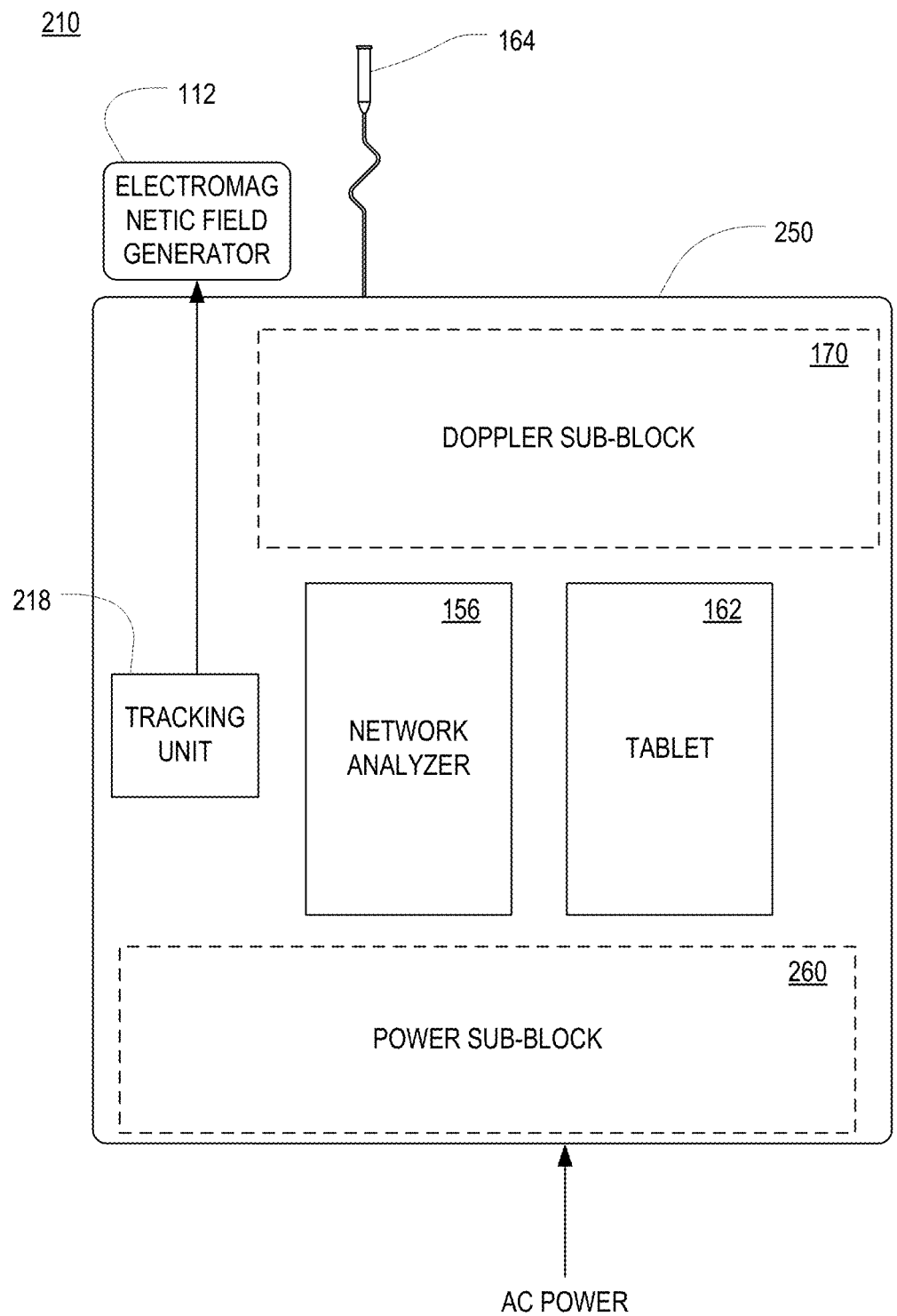
FIG. 8 is a block diagram of an EMFBioSI system containing an internal tracking unit.

FIG. 8 is a block diagram of an electromagnetic field bio-sensing and bio-imaging (EMFBioSI) system 210 in accordance with another preferred embodiment of the present invention. The system 210 is similar to that of FIG. 1, but has an internal tracking unit 218.

Figure 9:
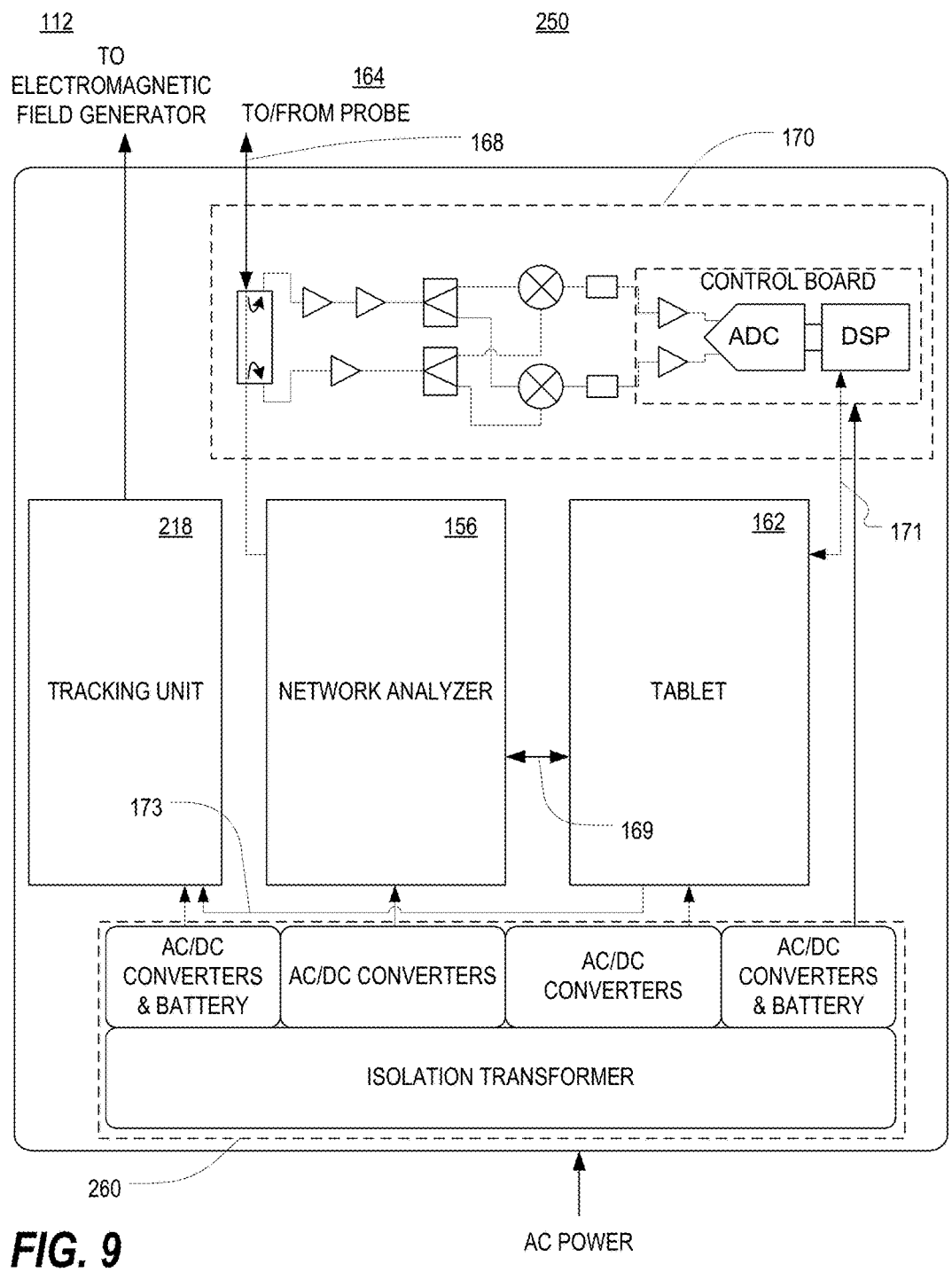
FIG. 9 is a block diagram of the handheld control unit of the system in FIG. 13.

FIG. 9 is a block diagram of the handheld control unit 250 of FIG. 8. The block diagram shows the internal tracking unit 218 and its connections to the AC/DC Converters and Battery in the Power Block 260 and to the Tablet 162.

Figure 10:
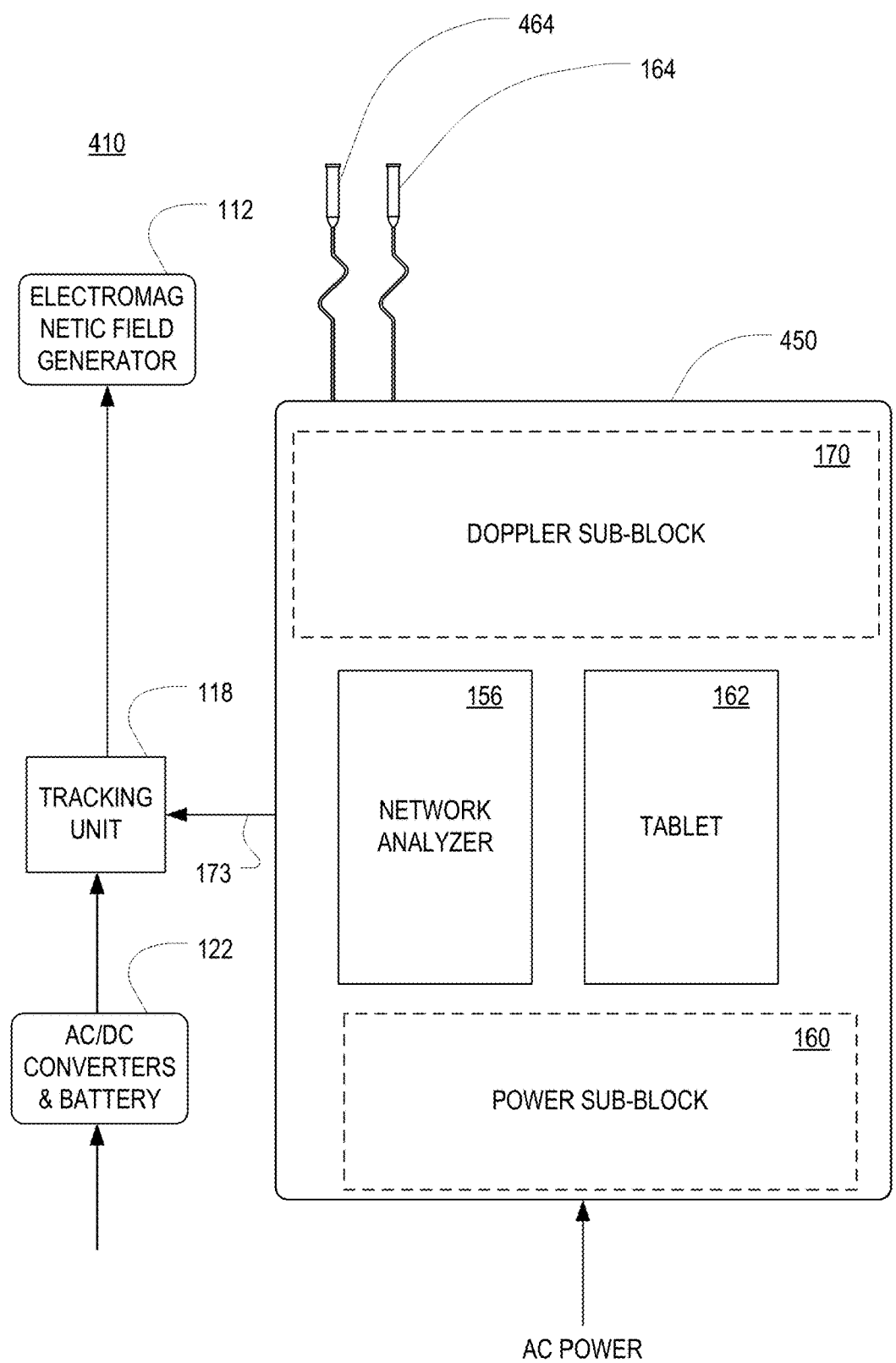
FIG. 10 is a block diagram of an EMFBioSI system in accordance with another preferred embodiment of the present invention.

FIG. 10 is a block diagram of an electromagnetic field bio-sensing and bio-imaging (EMFBioSI) system 410 in accordance with another preferred embodiment of the present invention. The system 410 is similar to that of FIG. 1, but having two probes 164.

Figure 11:
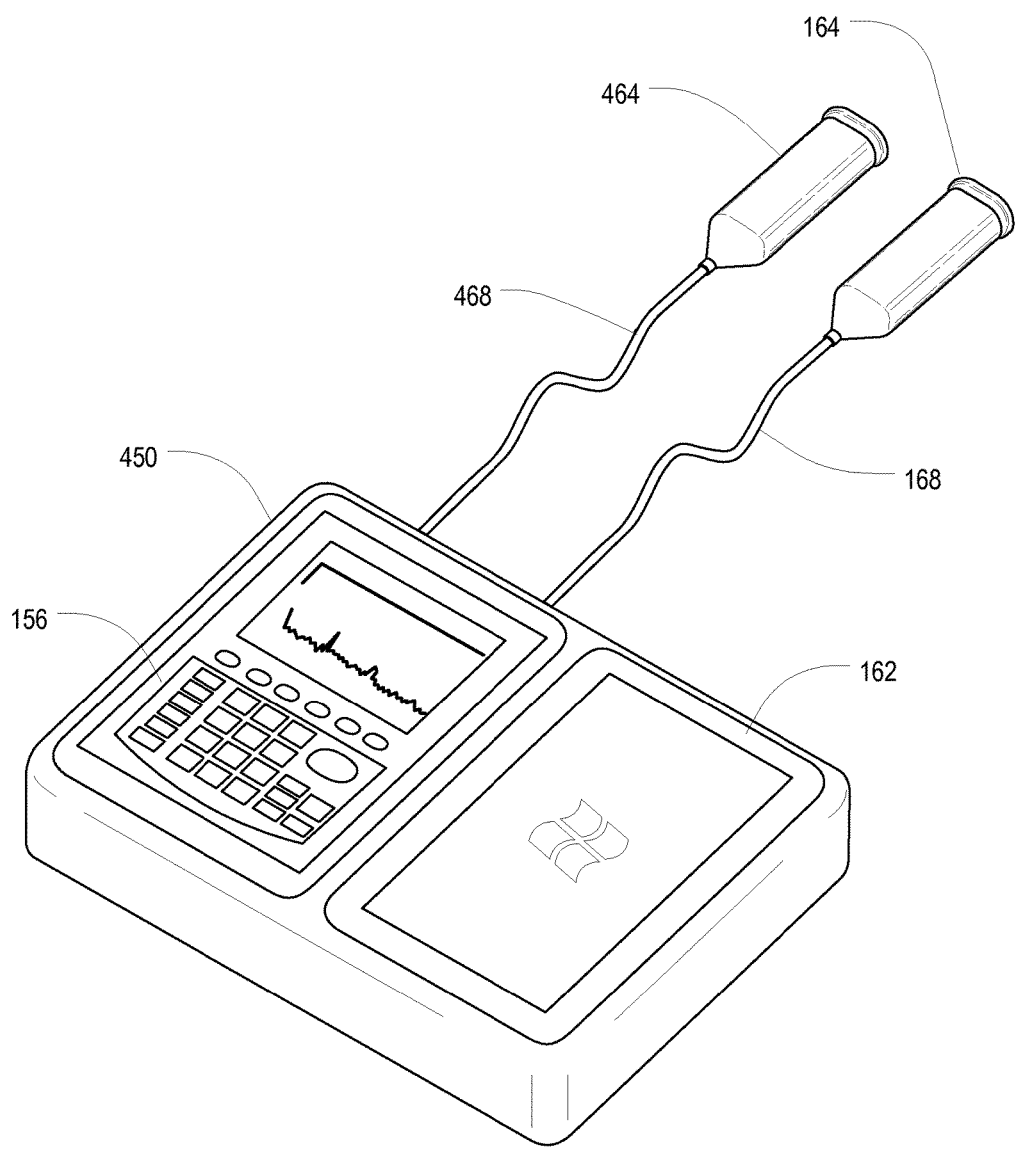
FIG. 11 is a perspective view of one possible implementation of the handheld control unit and probes of the system of FIG. 6.
Figure 12:
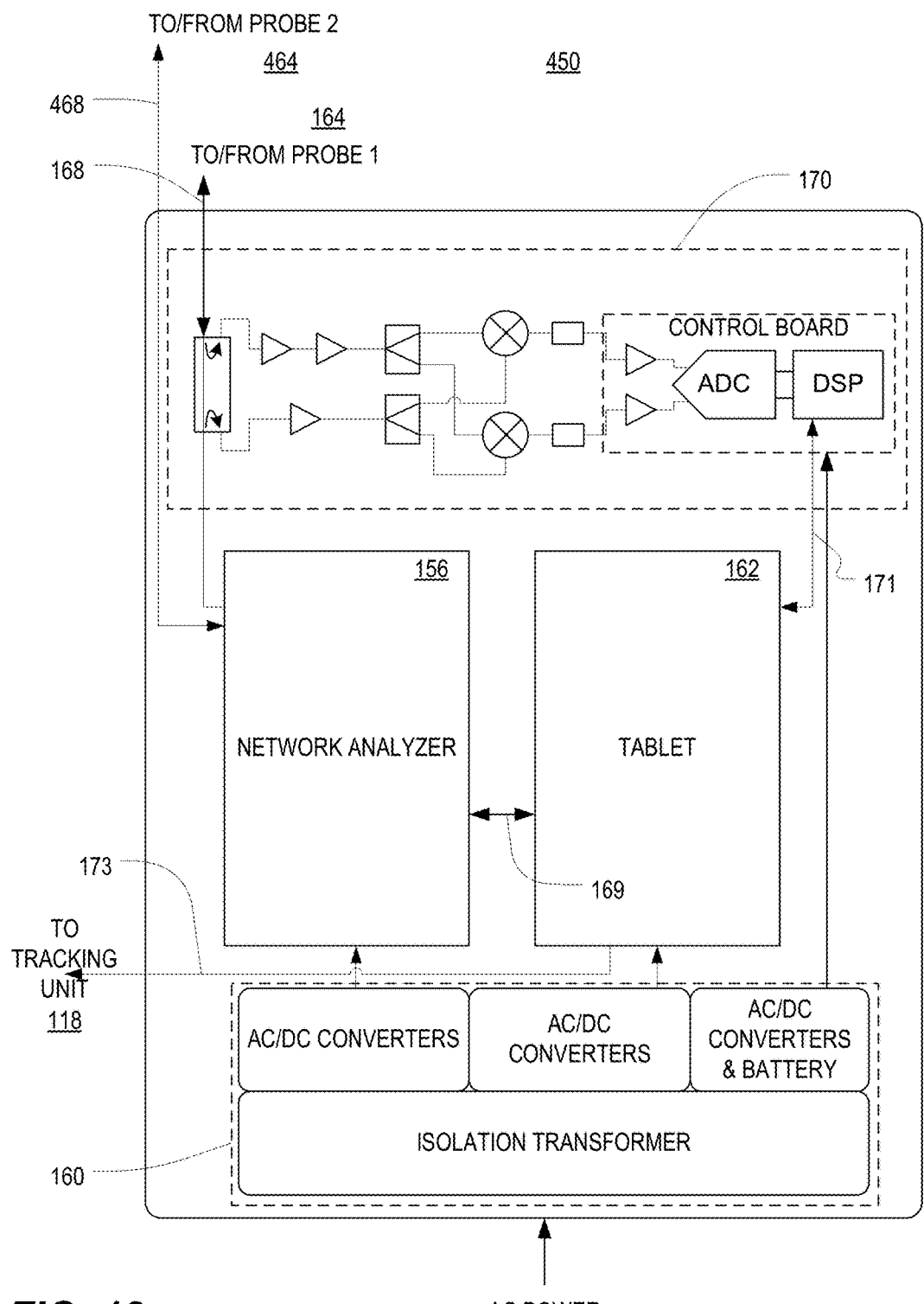
FIG. 12 is a block diagram of the handheld control unit of the system of FIG. 10.

FIG. 11 is a perspective view of the handheld control unit 450 and two probes 164, 464 of the EMFBioSI system 410, and FIG. 12 is a block diagram of the control unit 450 of FIG. 10. The control unit 450 is similar to that of FIG. 3, but having a second probe connection 468 to the second port of the VNA 156 for a second probe 464. In at least some embodiments, the probe connection 468 utilizes a high quality coaxial cable 468. As also described below, probe 1 164 and probe 2 464 both deliver and collect or receive EM signals after they pass through the interrogation region. After being received, they are processed by the Doppler sub-block 170, with the output being processed by an application on the tablet computer 162.

In this EMFBioSI system 410, because there are multiple probes, it is necessary to use signal indexing as described above. An EM signal received by one probe could have been transmitted by the same probe, or by a different probe. Thus, each received signal is sometimes referred to hereinafter as $S_{jk}$, where the index j refers to the jth port of the VNS that transmits the original electromagnetic signal from the VNA 156 via a cable and antenna in the probe 164 toward the interrogation zone, and the index k refers to the kth port of the VNA 156 that receives the reflected/scattered signal. In system 410, probe 1 164 irradiates an EM signal which is scattered by the tissue and then received by probe 1 164. As in system 110, the signal received by probe 1 is referred to as $S_{11}$. The EM signal irradiated by probe 1 164 may also be received by probe 2 464; if used, this signal is referred to as $S_{12}$. Furthermore, in the system 410 of FIG. 10, probe 2 464 may also irradiate an EM signal which is scattered by the tissue and then received by probe 1 164, probe 2 464, or both. A signal irradiated by probe 2 464 and received by probe 1 164 may be referred to as $S_{21}$; a signal both irradiated and received by probe 2 464 may be referred to as $S_{22}$.

Referring again to FIG. 12, probe 1 164 receives the reflected and scattered signals $S_{11}$ and $S_{21}$ from the arm tissue and returns a signal to the Doppler Sub-block 170 where processing continues through just as it does in system 110 and then the digitized signals on the ADC outputs 212,214 are provided to the DSP 220 or directly to a computer 162 for further signal analysis and processing. $S_{12}$ is received by the VNA 156 and passed through a connection to the tablet 162 for further analysis and processing.

Figure 13:
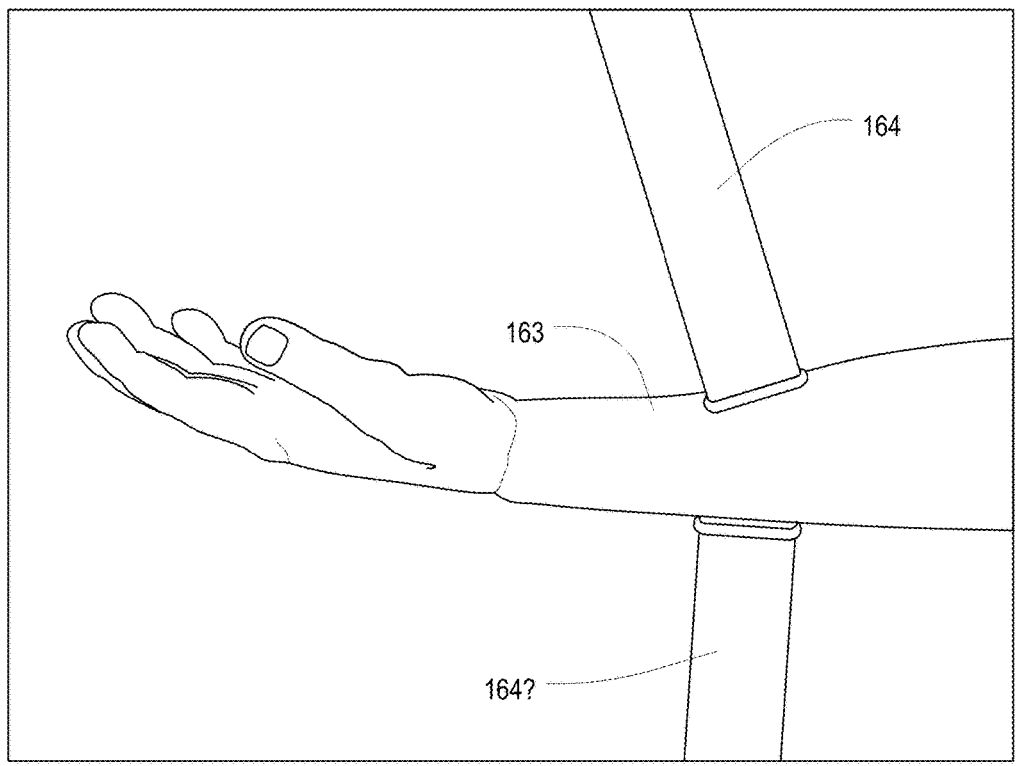
FIG. 13 is a perspective view of the two probes of FIG. 11 being placed on an arm.

FIG. 13 is a perspective view of the two probes 164,464 used in the EMFBioSI system 410, placed on an arm.

Figure 14:
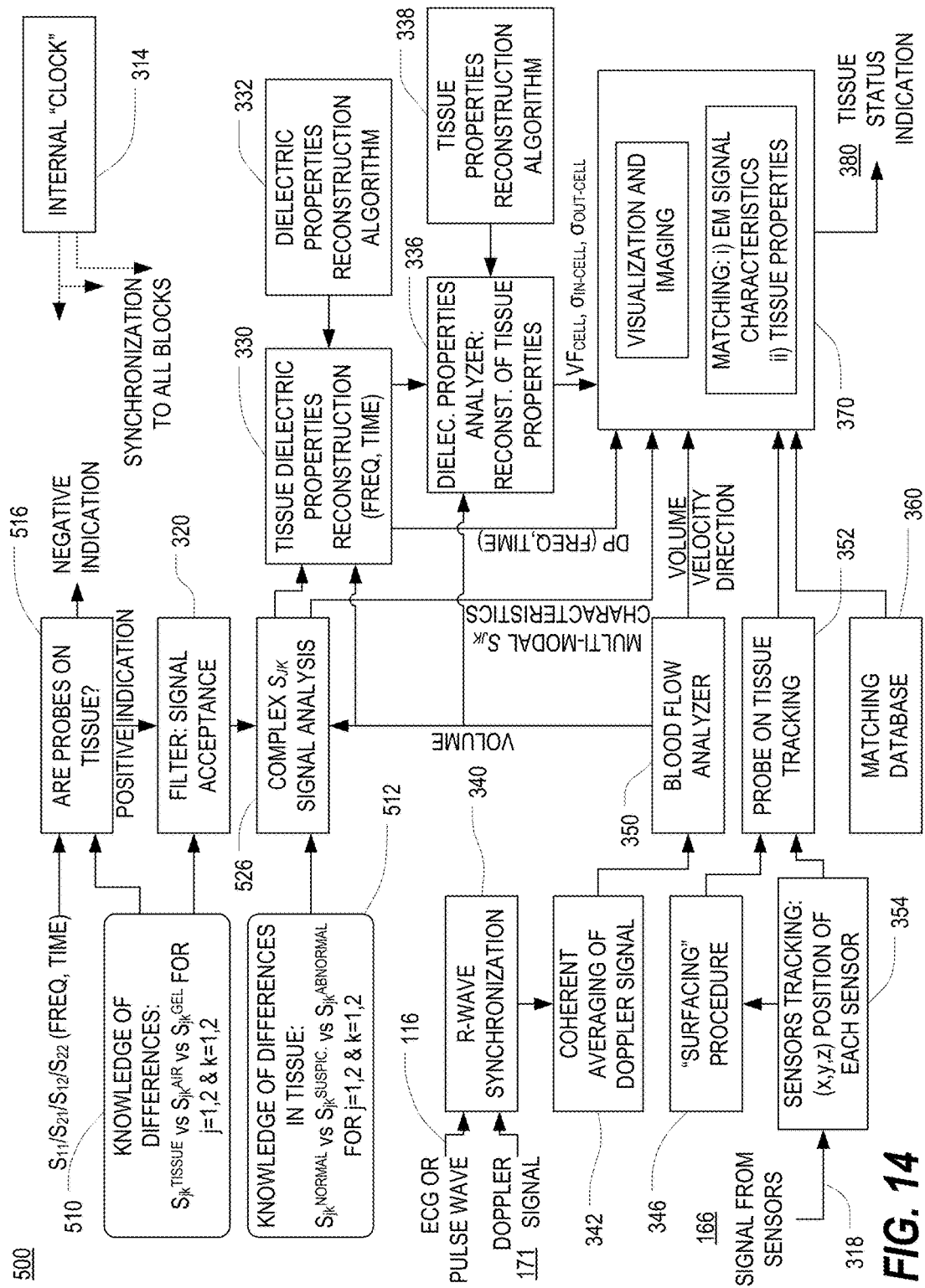
FIG. 14 is a flow diagram of the operational process of the EMFBioSI system of FIG. 10 in accordance with one or more preferred embodiments of the present invention.

FIG. 14 is a flow diagram of the operational process 500 of the EMFBioSI system 410 of FIG. 10 in accordance with one or more preferred embodiments of the present invention and is similar to the flow diagram of the operational process 300 with the differences detailed hereinbelow. As shown therein, this process 500 utilizes a number of input signals, including $S_{jk}$ (where j=1,2 and k=1,2); an internal clock 314; the output of the Doppler sub-block 170, introduced in FIG. 4; sensor signals 318, and an electrocardiography (ECG) or plethysmography signal 116. The process 500 also utilizes additional data and other information, obtained or derived prior to operation and stored in a database or elsewhere in the system 410. Such information, which serves as control data, includes material type information (control data) 510 pertaining to the how the characteristics of $S_{jk}$ vary based on whether $S_{jk}$ pass through tissue, air, or a gel, and tissue status information (control data) 512 pertaining to "normal," "suspicious," and "abnormal" characteristics of $S_{jk}$. Such material type information or control data 510 may be obtained via physical/biophysical experiments, while the tissue status information or control data 512 may be obtained during previous clinical procedures when a particular EM signal $S_{jk}$ is correlated with tissue pathological studies.

The material type control data 510 is used in a decision block 516 where it is determined whether both probes 164, 464 are on biologic tissue 163 or not. In order to facilitate ease of use by the operator, an indication of whether the probes 164, 464 are properly on the tissue 163 or not. Such an indication might include a green light, a beep, or the like. A corresponding indication when the probes 164, 464 are not on the tissue, such as a red light, a buzzer, or the like, may also be provided. The material type control data 510 is also provided as an input to a filter 320. Once it is determined the probes are on tissue 163 and the signal is within a valid range to pass the filter 320, the signal is ready for complex $S_{jk}$ signal analysis at block 526.

This block 526 also requires input from the tissue status control data 512 and a blood flow analyzer 350. The tissue status control data, which corresponds to the differences in the value of $S_{jk}$ resulting from normal, suspicious, or abnormal tissue, is stored in a computer database and is compared on-line with the received EM signal $S_{jk}$. Correlation and cross-correlation analysis as well as pattern recognition methods may be used.

The operational process 500 of the EMFBioSI system 410 of FIG. 10 receives input from position tracking sensors 166 located in probe 1 164 and probe 2 464. The information from these sensors 166 is needed in order to provide two dimensional and three-dimensional tissue surface mapping or tissue imaging, as the signal location and angle should be known for proper image reconstruction.

The operational process 300 culminates with visualization and imaging and matching analysis at block 370. Here, multi-modal $S_{jk}$ characteristics from the complex $S_{jk}$ signal analysis at block 326, dielectric property information based on frequency and time from the tissue dielectric properties reconstruction at block 330, tissue property information (such as $VF_{cell}$, $\sigma_{intracell}$, and $\sigma_{extracell}$) from the dielectric properties analyzer 336, blood flow information such as volume, velocity, and direction of blood flow from the blood flow analyzer 350, probe position information from the probe/tissue position tracker 352, and matching data from a matching database 360 are utilized to provide visualization and imaging of the tissue 163, and to match characteristics of the EM signals $S_{jk}$ to tissue properties in order to provide an indication 380 of tissue status to the operator.

Figure 15:
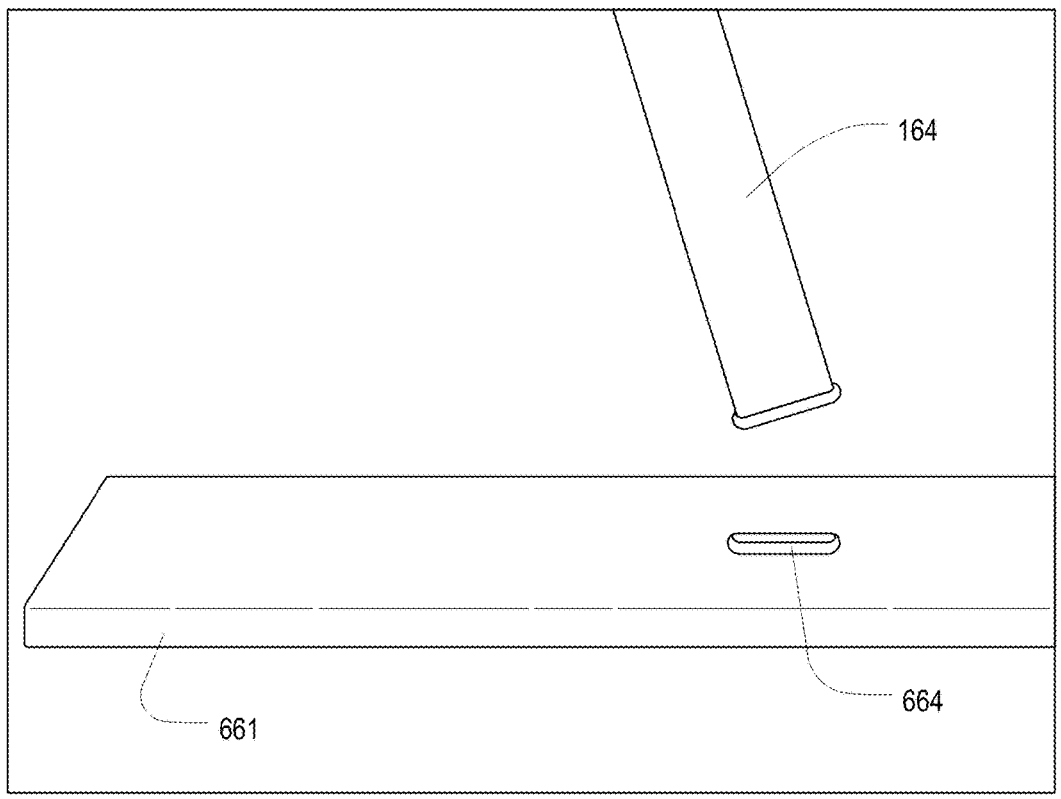
FIG. 15 is a perspective view of a probe combination in accordance with another preferred embodiment of the present invention.
Figure 16:
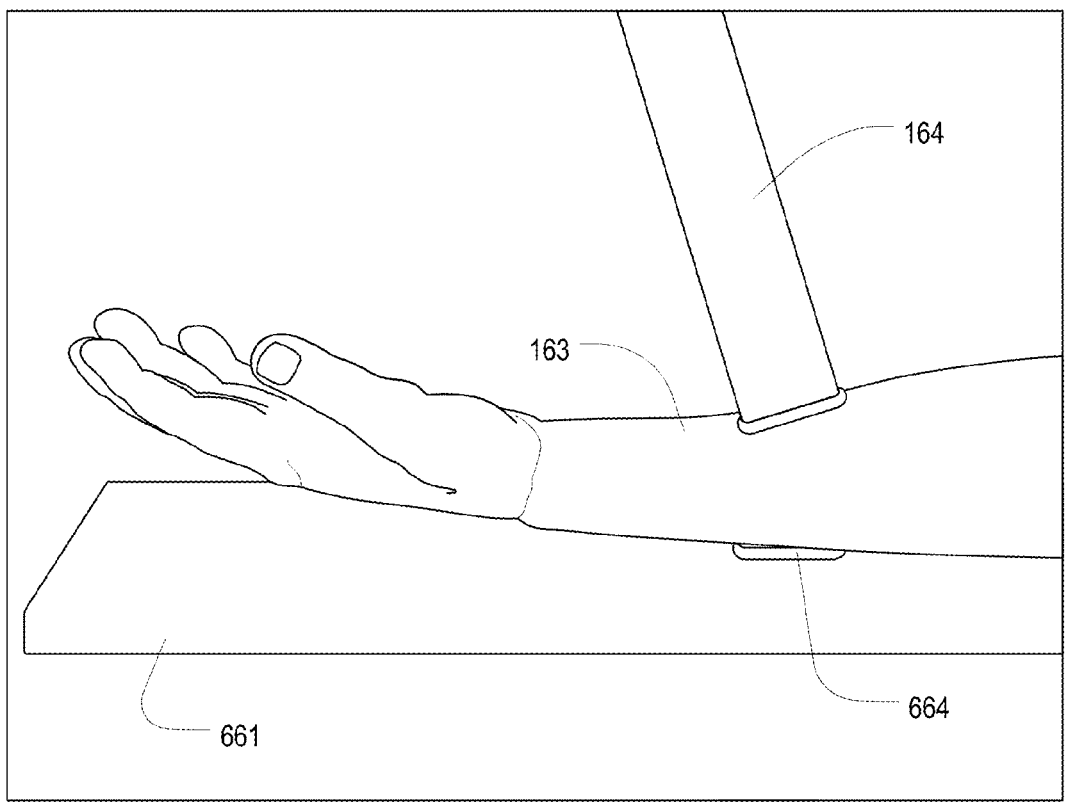
FIG. 16 is a perspective view of the probe of FIG. 15, being placed on a human arm.

FIG. 15 is a perspective view of a probe combination in accordance with another preferred embodiment of the present invention, and FIG. 16 is a perspective view of the probe of FIG. 15, being placed on a human arm. In this arrangement, a stationary probe, built into a stable base surface, such as a tabletop, serves as a second probe, thereby leaving the operator with a free hand while manipulating the first probe with his or her other hand. The position of the stationary probe relative to the stable base surface is thus defined. In at least most other respects, operation of this system is similar to the two probe implementation described previously.

Supporting Experimental Results

Figure 17A:
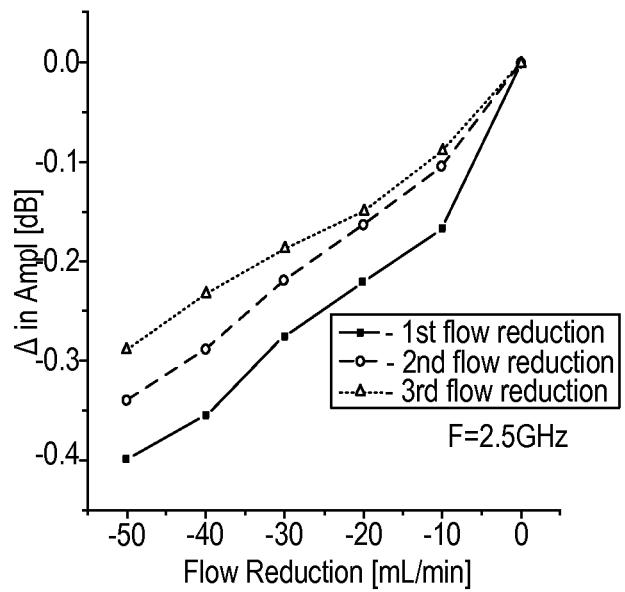
FIG. 17A is a graph showing the changes in amplitude of electromagnetic signals passed through a swine extremity due to a reduction in femoral artery blood flow.
Figure 17B:
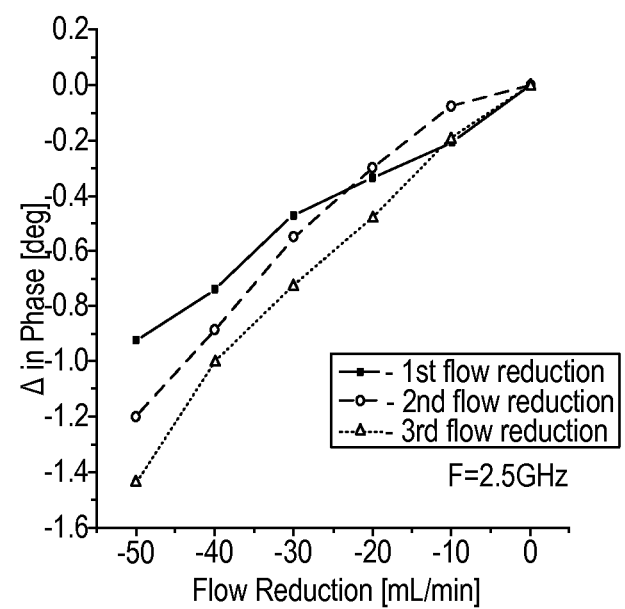
FIG. 17B is a graph showing the changes in phase of electromagnetic signals passed through a swine extremity due to a reduction in femoral artery blood flow.

FIG. 17A is a graph showing the changes in amplitude of Electromagnetic signals passed through a swine extremity due to a reduction in femoral blood flow. FIG. 17B is a graph showing the changes in phase of Electromagnetic signals passed through a swine extremity due to a reduction in femoral blood flow. These graphs show the results of three series of flow reduction (duration 2-3 minutes) through a swine thigh with 10 minute "wash out" periods in between series. A change in both the amplitude and the phase of electromagnetic signal was observed immediately after flow reduction. A linear correlation in amplitude and phase was also observed ($r^2 > 0.94$, $p > 0.001$). The technology demonstrates very high sensitivity being able to pick up flow reduction increments of as low as 2 [mL/min]. See Semenov S Y, Kellam J F, Althausen P, Williams T C, Abubakar A, Bulyshev A and Y Sizov, 2007 Microwave tomography for functional imaging of extremity soft tissues, Feasibility assessment Phys. Med. Biol., 52, 5705-19.

Figure 18A:
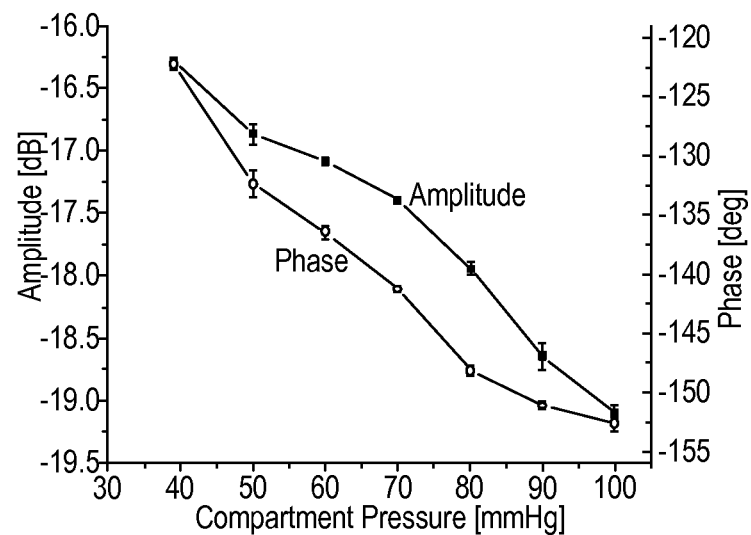
FIG. 18A is a graph showing the changes in amplitude and phase of electromagnetic signals passed through a swine extremity due to elevated compartmental pressure.
Figure 18B:
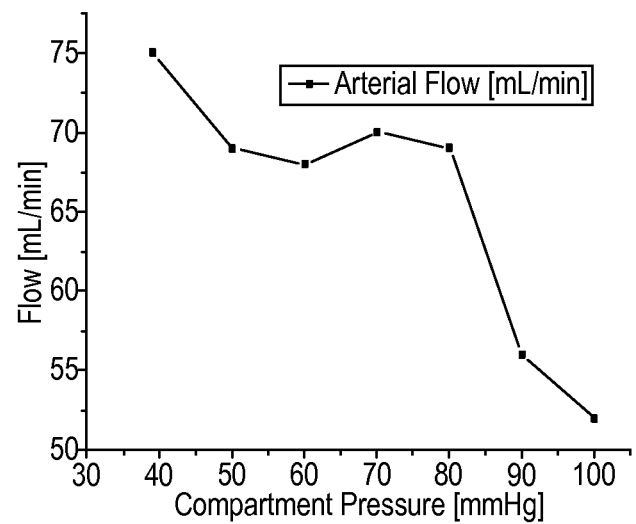
FIG. 18B is a graph showing the reduction in femoral blood flow due to elevated compartmental pressure in FIG. 18A.

FIG. 18A is a graph showing the changes in amplitude and phase of electromagnetic signals passed through a swine extremity due to elevated compartmental pressure. FIG. 18B is a graph showing the decrease in femoral blood flow due to elevated compartmental pressure in FIG. 18A. Excess of a fluid in the compartment, depending on the degree of extra-pressure, compromises arterial blood flow up to the point of a total occlusion, creating tissue ischemia/infarction. The frequency was 2.5 GHz.

Based on the foregoing information, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention.

Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements; the present invention being limited only by the claims appended hereto and the equivalents thereof.

What is claimed is:

1. A method of assessing status of a biological tissue, comprising:
   irradiating an electromagnetic signal, via a probe, into a biological tissue;
   receiving the irradiated electromagnetic signal after the signal is scattered/reflected by the biological tissue;
   providing blood flow information pertaining to the biological tissue;
   analyzing the received signal based at least upon the provided blood flow information and upon knowledge of electromagnetic signal differences in normal, suspicious, and abnormal tissue;
   providing results from the analyzing step to a dielectric properties reconstruction process;
   communicating at least some of the provided blood flow information to the dielectric properties reconstruction process;
   via the dielectric properties reconstruction process, reconstructing dielectric properties of the biological tissue based at least in part upon the results of the analyzing step;

providing results from the step of reconstructing dielectric properties to a tissue properties reconstruction process;

communicating at least some of the provided blood flow information to the tissue properties reconstruction process; and via the tissue properties reconstruction process, reconstructing tissue properties of the biological tissue based at least in part upon the results of the reconstructing step.

2. The method of claim 1, further comprising:

a preliminary step of determining whether the probe is in the vicinity of the biological tissue, such step being based at least in part upon knowledge of electromagnetic signal differences in biological tissue, air, and a gel; and a step of providing an indication, via the probe, as to whether the probe is determined to be in the vicinity of the biological tissue.

3. The method of claim 1, wherein receiving the irradiated electromagnetic signal includes receiving the irradiated electromagnetic signal at a probe.

4. The method of claim 3, further comprising a step of determining, via a tracking unit, the position of the probe that receives the irradiated electromagnetic signal while the step of receiving is being carried out.

5. The method of claim 4, further comprising:

a step of correlating the determined position of the probe to known information about the position and contours of the biological tissue; and a surfacing process, carried out prior to the step of receiving the irradiated electromagnetic signal, wherein the position of the probe, in at least two dimensions, is repeatedly determined as the probe is placed in different locations against the surface of the biological tissue, thereby developing a digital map of the surface of the biological tissue that is subsequently used in the correlating step.

6. The method of claim 1, wherein the blood flow information is provided at least partly on the basis of a step of synchronizing the received electromagnetic signal with a signal representing a blood circulation cycle of the biological tissue.

7. The method of claim 6, wherein the blood flow information is provided at least partly on the basis of a step, after the synchronizing step, of processing the synchronized signals using coherent averaging.

8. The method of claim 6, wherein the step of providing the blood flow information includes providing blood volume information.

9. The method of claim 1, wherein the irradiated electromagnetic signal is a first electromagnetic signal, wherein the received electromagnetic signal is a second electromagnetic signal and wherein the method further comprises a step of processing the first and second electromagnetic signals using a Doppler sub-block.

10. The method of claim 9, wherein the blood flow information is provided at least partly on the basis of a step of synchronizing an output of the Doppler sub-block with a signal representing a blood circulation cycle of the biological tissue.

11. The method of claim 1, wherein the step of analyzing the received signal includes a preliminary step of obtaining the knowledge of electromagnetic signal differences in normal, suspicious, and abnormal tissue during clinical procedures.

12. The method of claim 1, wherein the step of reconstructing tissue properties of the biological tissue includes reconstructing cellular volume fraction ($VF_{cell}$).

13. The method of claim 1, wherein the step of reconstructing tissue properties of the biological tissue includes reconstructing intracellular conductivity ($\sigma_{intracell}$).

14. The method of claim 1, wherein the step of reconstructing tissue properties of the biological tissue includes reconstructing extracellular conductivity ($\sigma_{extracell}$).

15. The method of claim 1, further comprising a step, after the step of reconstructing tissue properties of the biological tissue, of conducting visualization, imaging and matching analysis.

16. The step of claim 15, wherein the step of conducting visualization, imaging and matching analysis is based at least in part upon results of the step of reconstructing dielectric properties of the biological tissue.

17. The method of claim 16, wherein dielectric property information based on frequency is an input to the step of conducting visualization, imaging and matching analysis.

18. The method of claim 16, wherein dielectric property information based on time is an input to the step of conducting visualization, imaging and matching analysis.

19. The method of claim 15, wherein the step of conducting visualization, imaging and matching analysis is based at least in part upon results of the step of providing the blood flow information.

20. The method of claim 4, wherein the step of determining the position of the probe includes determining the position of at least three sensors disposed and spatially separated within the probe that receives the irradiated electromagnetic signal, and wherein the step of determining the position of the probe includes determining the position of the probe in three dimensions.

* * * * *